(12) United States Patent
Lawes et al.

(10) Patent No.: US 7,160,298 B2
(45) Date of Patent: Jan. 9, 2007

(54) ELECTROSURGICAL INSTRUMENT WHICH REDUCES EFFECTS TO ADJACENT TISSUE STRUCTURES

(75) Inventors: Kate R. Lawes, Superior, CO (US); Steven P. Buysse, Longmont, CO (US); Sean T. Dycus, Denver, CO (US); Kristin D. Johnson, Louisville, CO (US); Michael C. Moses, Boulder, CO (US); David A. Schechter, Longmont, CO (US); Philip M. Tetzlaff, Superior, CO (US); Carolyn H. Mihaichuk, Erie, CO (US)

(73) Assignee: Sherwood Services AG, Schaffhausen (CH)

( * ) Notice: Subject to any disclaimer, the term of this patent is extended or adjusted under 35 U.S.C. 154(b) by 295 days.

(21) Appl. No.: 10/474,273

(22) PCT Filed: Apr. 6, 2001

(86) PCT No.: PCT/US01/11230

§ 371 (c)(1),
(2), (4) Date: Oct. 3, 2003

(87) PCT Pub. No.: WO02/080784

PCT Pub. Date: Oct. 17, 2002

(65) Prior Publication Data
US 2005/0004568 A1  Jan. 6, 2005

Related U.S. Application Data

(63) Continuation-in-part of application No. 09/387,883, filed on Sep. 1, 1999, now abandoned, which is a continuation of application No. 08/968,496, filed on Nov. 12, 1997, now Pat. No. 6,050,996.

(51) Int. Cl.
*A61B 18/18* (2006.01)

(52) U.S. Cl. .......................................... 606/51; 606/50
(58) Field of Classification Search ............. 606/45–52
See application file for complete search history.

(56) References Cited

U.S. PATENT DOCUMENTS

| 371,664 A | 10/1887 | Brannan et al. |
| 702,472 A | 6/1902 | Pignolet |
| 728,883 A | 5/1903 | Downes |

(Continued)

FOREIGN PATENT DOCUMENTS

CA  2104423  2/1994

(Continued)

OTHER PUBLICATIONS

Sigel et al. "The Mechanism of Blood Vessel Closure by High Frequency Electrocoagulation" Surgery Gynecology & Obstetrics, Oct. 1965, pp. 823-831.

(Continued)

*Primary Examiner*—Michael Peffley

(57) ABSTRACT

An electrosurgical instrument which includes opposing end effectors and a handle for effecting movement of the end effectors relative to one another. The instrument includes a housing and a pair of electrodes. Each elecdode preferably includes an electrically conductive surface (e.g., which can be dimensioned for sealing, clamping and/or cutting) and an insulating substrate which is dimensioned to be engageable with the end effectors such that the electrodes reside in opposing relation relative to one another. The dimensions of the insulating substrate are different from the dimensions of the electrically conductive surface to reduce thermal spread to adjacent tissue structures. The insulating substrate is made from a material having a Comparative Tracking Index of about 300 volts to about 600 volts to reduce the incidence of flashover.

9 Claims, 18 Drawing Sheets

U.S. PATENT DOCUMENTS

| | | |
|---|---|---|
| 1,586,645 A | 6/1926 | Bierman |
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,862,630 A | 1/1975 | Balamuth |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 4,005,714 A | 2/1977 | Hiltebrandt |
| 4,041,952 A | 8/1977 | Morrison, Jr. et al. |
| 4,074,718 A | 2/1978 | Morrison, Jr. |
| 4,088,134 A | 5/1978 | Mazzariello |
| 4,128,099 A | 12/1978 | Bauer |
| 4,165,746 A | 8/1979 | Burgin |
| 4,300,564 A | 11/1981 | Furihata |
| 4,370,980 A | 2/1983 | Lottick |
| 4,416,276 A | 11/1983 | Newton et al. |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,763,669 A | 8/1988 | Jaeger |
| 4,827,929 A | 5/1989 | Hodge |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| 5,330,471 A | 7/1994 | Eggers |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,423,810 A | 6/1995 | Goble et al. |
| 5,425,739 A | 6/1995 | Jessen |
| 5,429,616 A | 7/1995 | Schaffer |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,542,945 A | 8/1996 | Fritzsch |
| 5,558,672 A | 9/1996 | Edwards et al. |
| 5,562,699 A | 10/1996 | Heimberger et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,582,611 A | 12/1996 | Tsukagoshi et al. |
| 5,585,896 A | 12/1996 | Yamazaki et al. |
| 5,590,570 A | 1/1997 | LeMaire, III et al. |
| 5,601,601 A | 2/1997 | Tal et al. |
| 5,603,711 A | 2/1997 | Parins et al. |
| 5,603,723 A | 2/1997 | Aranyi et al. |

| | | | | | | |
|---|---|---|---|---|---|---|
| 5,611,798 A | 3/1997 | Eggers | | 5,976,132 A | 11/1999 | Morris |
| 5,626,578 A | 5/1997 | Tihon | | 5,984,939 A | 11/1999 | Yoon |
| 5,626,609 A | 5/1997 | Zvenyatsky et al. | | 5,989,277 A | 11/1999 | LeMaire, III et al. |
| 5,630,833 A | 5/1997 | Katsaros et al. | | 6,004,335 A | 12/1999 | Vaitekunas et al. |
| 5,637,110 A | 6/1997 | Pennybacker et al. | | 6,010,516 A | 1/2000 | Hulka et al. |
| 5,643,294 A | 7/1997 | Tovey et al. | | 6,024,741 A | 2/2000 | Willaimson et al. |
| 5,647,869 A | 7/1997 | Goble et al. | | 6,024,744 A | 2/2000 | Kese et al. |
| 5,647,871 A | 7/1997 | Levine et al. | | 6,033,399 A | 3/2000 | Gines |
| 5,649,959 A | 7/1997 | Hannam et al. | | 6,039,733 A | 3/2000 | Buysse et al. |
| 5,658,281 A | 8/1997 | Heard | | 6,041,679 A | 3/2000 | Slater et al. |
| 5,662,667 A | 9/1997 | Knodel | | 6,050,996 A | 4/2000 | Schmaltz et al. |
| 5,665,100 A | 9/1997 | Yoon | | 6,053,914 A | 4/2000 | Eggers et al. |
| 5,667,526 A | 9/1997 | Levin | | 6,053,933 A | 4/2000 | Balazs et al. |
| 5,674,220 A * | 10/1997 | Fox et al. ................ 606/51 | | D424,694 S | 5/2000 | Tetzlaff et al. |
| 5,681,282 A | 10/1997 | Eggers et al. | | D425,201 S | 5/2000 | Tetzlaff et al. |
| 5,693,051 A | 12/1997 | Schulze et al. | | 6,059,782 A | 5/2000 | Novak et al. |
| 5,695,522 A | 12/1997 | LeMaire, III et al. | | RE36,795 E | 7/2000 | Rydell |
| 5,700,261 A | 12/1997 | Brinkerhoff | | 6,083,223 A | 7/2000 | Baker |
| 5,702,390 A | 12/1997 | Austin et al. | | 6,086,586 A * | 7/2000 | Hooven ................ 606/50 |
| 5,707,369 A | 1/1998 | Vaitekunas et al. | | 6,090,107 A | 7/2000 | Borgmeier et al. |
| 5,709,680 A | 1/1998 | Yates et al. | | 6,096,031 A | 8/2000 | Mitchell et al. |
| 5,716,366 A | 2/1998 | Yates | | 6,096,037 A | 8/2000 | Mulier et al. |
| 5,727,428 A | 3/1998 | LeMaire, III et al. | | 6,099,550 A | 8/2000 | Yoon |
| 5,735,848 A | 4/1998 | Yates et al. | | 6,102,909 A | 8/2000 | Chen et al. |
| 5,743,906 A | 4/1998 | Parins et al. | | 6,110,171 A | 8/2000 | Rydell |
| 5,755,717 A | 5/1998 | Yates et al. | | 6,113,596 A | 9/2000 | Hooven et al. |
| 5,766,130 A | 6/1998 | Selmonosky | | 6,113,598 A | 9/2000 | Baker |
| 5,766,166 A | 6/1998 | Hooven | | 6,117,158 A | 9/2000 | Measamer et al. |
| 5,766,170 A | 6/1998 | Eggers | | 6,123,701 A | 9/2000 | Nezhat |
| 5,769,849 A | 6/1998 | Eggers | | H1904 H | 10/2000 | Yates et al. |
| 5,772,655 A | 6/1998 | Bauer et al. | | 6,126,658 A | 10/2000 | Baker |
| 5,772,670 A | 6/1998 | Brosa | | 6,152,923 A | 11/2000 | Ryan |
| 5,776,128 A | 7/1998 | Eggers | | 6,174,309 B1 | 1/2001 | Wrublewski et al. |
| 5,776,130 A | 7/1998 | Buysse et al. | | 6,179,834 B1 | 1/2001 | Buysse et al. |
| 5,779,701 A | 7/1998 | McBrayer et al. | | 6,179,837 B1 | 1/2001 | Hooven |
| 5,792,137 A | 8/1998 | Carr et al. | | 6,183,467 B1 | 2/2001 | Shapeton et al. |
| 5,792,177 A | 8/1998 | Kaseda | | 6,187,003 B1 | 2/2001 | Buysse et al. |
| 5,797,938 A | 8/1998 | Paraschac et al. | | 6,190,386 B1 | 2/2001 | Rydell |
| 5,797,958 A | 8/1998 | Yoon | | 6,193,718 B1 | 2/2001 | Kortenbach et al. |
| 5,800,449 A | 9/1998 | Wales | | 6,206,876 B1 | 3/2001 | Levine et al. |
| 5,807,393 A | 9/1998 | Williamson, IV et al. | | 6,206,877 B1 | 3/2001 | Kese et al. |
| 5,810,808 A | 9/1998 | Eggers | | 6,217,602 B1 | 4/2001 | Redmon |
| 5,810,811 A * | 9/1998 | Yates et al. ............. 606/50 | | 6,224,593 B1 | 5/2001 | Ryan et al. |
| 5,810,877 A | 9/1998 | Roth et al. | | 6,228,080 B1 | 5/2001 | Gines |
| 5,814,043 A | 9/1998 | Shapeton | | 6,228,083 B1 | 5/2001 | Lands et al. |
| 5,820,630 A | 10/1998 | Lind | | 6,267,761 B1 | 7/2001 | Ryan |
| 5,827,271 A | 10/1998 | Buysse et al. | | 6,270,497 B1 | 8/2001 | Sekino et al. |
| 5,827,279 A | 10/1998 | Hughett et al. | | 6,270,508 B1 | 8/2001 | Klieman et al. |
| 5,827,281 A | 10/1998 | Levin | | 6,273,887 B1 | 8/2001 | Yamauchi et al. |
| 5,833,690 A | 11/1998 | Yates et al. | | 6,277,117 B1 | 8/2001 | Tetzlaff et al. |
| 5,843,080 A | 12/1998 | Fleenor et al. | | 6,280,458 B1 | 8/2001 | Boche et al. |
| 5,849,022 A | 12/1998 | Sakashita et al. | | 6,283,961 B1 | 9/2001 | Underwood et al. |
| 5,853,412 A | 12/1998 | Mayenberger | | D449,886 S | 10/2001 | Tetzlaff et al. |
| 5,860,976 A | 1/1999 | Billings et al. | | 6,322,561 B1 | 11/2001 | Eggers et al. |
| 5,876,401 A | 3/1999 | Schulze et al. | | 6,334,860 B1 | 1/2002 | Dorn |
| 5,891,141 A | 4/1999 | Rydell | | 6,334,861 B1 | 1/2002 | Chandler et al. |
| 5,891,142 A | 4/1999 | Eggers et al. | | 6,350,264 B1 | 2/2002 | Hooven |
| 5,893,863 A | 4/1999 | Yoon | | 6,352,536 B1 | 3/2002 | Buysse et al. |
| 5,893,875 A | 4/1999 | O'Connor et al. | | D457,958 S | 5/2002 | Dycus et al. |
| 5,893,877 A | 4/1999 | Gampp, Jr. et al. | | D457,959 S | 5/2002 | Tetzlaff et al. |
| 5,902,301 A | 5/1999 | Olig | | 6,387,094 B1 | 5/2002 | Eitenmuller |
| 5,906,630 A | 5/1999 | Anderhub et al. | | 6,398,779 B1 | 6/2002 | Buysse et al. |
| 5,908,420 A | 6/1999 | Parins et al. | | 6,402,747 B1 | 6/2002 | Lindemann et al. |
| 5,911,719 A | 6/1999 | Eggers | | 6,409,728 B1 | 6/2002 | Ehr et al. |
| 5,913,874 A | 6/1999 | Berns et al. | | H2037 H | 7/2002 | Yates et al. |
| 5,921,984 A | 7/1999 | Sutcu et al. | | 6,419,675 B1 | 7/2002 | Gallo, Sr. |
| 5,925,043 A | 7/1999 | Kumar et al. | | 6,425,896 B1 | 7/2002 | Baltschun et al. |
| 5,935,126 A | 8/1999 | Riza | | 6,443,952 B1 | 9/2002 | Mulier et al. |
| 5,944,718 A | 8/1999 | Dafform et al. | | 6,443,970 B1 | 9/2002 | Schulze et al. |
| 5,951,549 A | 9/1999 | Richardson et al. | | 6,451,018 B1 | 9/2002 | Lands et al. |
| 5,954,720 A | 9/1999 | Wilson et al. | | 6,458,128 B1 | 10/2002 | Schulze |
| 5,957,923 A | 9/1999 | Hahnen et al. | | 6,458,130 B1 | 10/2002 | Frazier et al. |
| 5,961,514 A | 10/1999 | Long et al. | | 6,464,701 B1 | 10/2002 | Hooven et al. |

| | | | |
|---|---|---|---|
| 6,464,704 B1 | 10/2002 | Schmaltz et al. | |
| 6,503,248 B1 | 1/2003 | Levine | |
| 6,506,189 B1 | 1/2003 | Rittman, III et al. | |
| 6,511,480 B1 | 1/2003 | Tetzlaff et al. | |
| 6,514,251 B1 | 2/2003 | Ni et al. | |
| 6,544,264 B1 | 4/2003 | Levine et al. | |
| 6,569,162 B1 | 5/2003 | He | |
| 6,585,735 B1 | 7/2003 | Frazier et al. | |
| 6,620,161 B1 | 9/2003 | Schulze et al. | |
| 6,652,521 B1 | 11/2003 | Schulze | |
| 6,656,177 B1 | 12/2003 | Truckai et al. | |
| 6,669,696 B1 | 12/2003 | Bacher et al. | |
| 6,682,528 B1 | 1/2004 | Frazier et al. | |
| 6,685,724 B1 | 2/2004 | Haluck | |
| 6,733,498 B1 | 5/2004 | Paton et al. | |
| 6,743,229 B1 | 6/2004 | Buysse et al. | |
| 6,773,434 B1 | 8/2004 | Ciarrocca | |
| 6,776,780 B1 | 8/2004 | Mulier et al. | |
| D496,997 S | 10/2004 | Dycus et al. | |
| 6,802,843 B1 | 10/2004 | Truckai et al. | |
| D499,181 S | 11/2004 | Dycus et al. | |
| 6,818,000 B1 | 11/2004 | Muller et al. | |
| 6,926,716 B1 | 8/2005 | Baker et al. | |
| 6,929,644 B1 | 8/2005 | Truckai et al. | |
| 6,942,662 B1 | 9/2005 | Goble et al. | |
| 6,964,662 B1 | 11/2005 | Kidooka | |
| 2002/0013583 A1 | 1/2002 | Camran et al. | |
| 2002/0099372 A1 | 7/2002 | Schulze et al. | |
| 2002/0107517 A1 | 8/2002 | Witt et al. | |
| 2002/0111624 A1 | 8/2002 | Witt et al. | |
| 2002/0188294 A1 | 12/2002 | Couture et al. | |
| 2003/0018331 A1 | 1/2003 | Dycus et al. | |
| 2003/0069571 A1 | 4/2003 | Treat et al. | |
| 2003/0078578 A1 | 4/2003 | Truckai et al. | |
| 2003/0139741 A1 | 7/2003 | Goble et al. | |
| 2003/0139742 A1 | 7/2003 | Wampler et al. | |
| 2003/0158549 A1 | 8/2003 | Swanson | |
| 2003/0199869 A1 | 10/2003 | Johnson et al. | |
| 2003/0216732 A1 | 11/2003 | Truckai et al. | |
| 2003/0220637 A1 | 11/2003 | Truckai et al. | |
| 2003/0236325 A1 | 12/2003 | Bonora | |
| 2004/0030330 A1 | 2/2004 | Brassell et al. | |
| 2004/0030332 A1 | 2/2004 | Knowlton et al. | |
| 2004/0049185 A1 | 3/2004 | Latterell et al. | |
| 2004/0116979 A1 | 6/2004 | Truckai et al. | |
| 2004/0147925 A1 | 7/2004 | Buysse et al. | |
| 2004/0225288 A1 | 11/2004 | Buysse et al. | |
| 2004/0230189 A1 | 11/2004 | Keppel | |
| 2004/0236325 A1 | 11/2004 | Tetzlaff et al. | |
| 2004/0243125 A1 | 12/2004 | Dycus et al. | |
| 2004/0249371 A1 | 12/2004 | Dycus et al. | |
| 2004/0249374 A1 | 12/2004 | Tetzlaff et al. | |
| 2004/0250419 A1 | 12/2004 | Sremcich et al. | |
| 2004/0254573 A1 | 12/2004 | Dycus et al. | |
| 2005/0004564 A1 | 1/2005 | Wham et al. | |
| 2005/0004568 A1 | 1/2005 | Lawes et al. | |
| 2005/0004570 A1 | 1/2005 | Chapman et al. | |
| 2005/0021025 A1 | 1/2005 | Buysse et al. | |
| 2005/0021026 A1 | 1/2005 | Baily | |
| 2005/0021027 A1 | 1/2005 | Shields et al. | |
| 2005/0033278 A1 | 2/2005 | McClurken et al. | |
| 2005/0101951 A1 | 5/2005 | Wham et al. | |
| 2005/0101952 A1 | 5/2005 | Lands et al. | |
| 2005/0107784 A1 | 5/2005 | Moses et al. | |
| 2005/0107785 A1 | 5/2005 | Dycus et al. | |
| 2005/0113818 A1 | 5/2005 | Sartor et al. | |
| 2005/0113819 A1 | 5/2005 | Wham et al. | |
| 2005/0113826 A1 | 5/2005 | Johnson et al. | |
| 2005/0113827 A1 | 5/2005 | Dumbauld et al. | |
| 2005/0113828 A1 | 5/2005 | Shields et al. | |
| 2005/0119855 A1 | 6/2005 | Moses et al. | |
| 2005/0149151 A1 | 7/2005 | Orszulak et al. | |
| 2006/0079891 A1 | 4/2006 | Arts et al. | |

FOREIGN PATENT DOCUMENTS

| | | |
|---|---|---|
| DE | 2415263 | 10/1975 |
| DE | 8712328 | 3/1988 |
| DE | 29616210 | 1/1997 |
| DE | 19608716 | 4/1997 |
| DE | 19751108 | 5/1999 |
| EP | 0364216 A1 | 4/1990 |
| EP | 518230 A1 | 12/1992 |
| EP | 0 541 930 B1 | 5/1993 |
| EP | 0572131 | 12/1993 |
| EP | 0572131 A1 | 12/1993 |
| EP | 584787 A1 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1330991 A1 | 7/2003 |
| EP | 1486177 A2 | 6/2004 |
| EP | 1532932 A1 | 5/2005 |
| GB | 2214430 A | 6/1989 |
| JP | 501068 | 9/1984 |
| JP | 502328 | 3/1992 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 | 11/1974 |
| WO | WO 92/06642 | 4/1992 |
| WO | WO 94/08524 A | 4/1994 |
| WO | WO 95/02369 | 1/1995 |
| WO | WO 95/07662 | 3/1995 |
| WO | WO 96/022056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |

| | | |
|---|---|---|
| WO | WO 99/12488 A | 3/1999 |
| WO | WO 99/40857 | 8/1999 |
| WO | WO 99/040861 | 8/1999 |
| WO | WO 99/51158 | 10/1999 |
| WO | WO 99/066850 | 12/1999 |
| WO | WO 99/66850 A | 12/1999 |
| WO | WO 00/24330 | 5/2000 |
| WO | WO 00/24331 | 5/2000 |
| WO | WO 00/41638 | 7/2000 |
| WO | WO 00/53112 | 9/2000 |
| WO | WO 01/17448 A | 3/2001 |
| WO | WO 01/54604 | 8/2001 |
| WO | WO 01/54604 A1 | 8/2001 |
| WO | WO 02/07627 | 1/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/101311 | 12/2003 |
| WO | WO 04/032777 | 4/2004 |
| WO | WO 2004/052221 A1 | 6/2004 |
| WO | WO 04/073490 | 9/2004 |
| WO | WO 04/082495 | 9/2004 |
| WO | WO 2004/082495 A1 | 9/2004 |
| WO | WO 2004/098383 A1 | 11/2004 |
| WO | WO 04/103156 | 12/2004 |

OTHER PUBLICATIONS

Bergdahl et al. "Studies on Coagulation and the Development of an Automatic Computerized Bipolar Coagulator" J. Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics Figo World Congress 2000, Washington, D.C.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
Int'l Search Report PCT/US01/11218.
Int'l Search Report PCT/US99/24869.
Int'l Search Report PCT/US98/18640.
Int'l Search Report PCT/US98/23950.

Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With The LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
International Search Report PCT/US01/11340.
International Search Report PCT/US01/11420.
International Search Report PCT/US02/01890.
International Search Report PCT/US02/11100.
International Search Report PCT/US04/03436.
International Search Report PCT/US04/13273.
International Search Report PCT/US04/15311.
International Search Report EP 98944778.
International Search Report EP 98958575.
International Search Report EP 04027479.
International Search Report EP 04027705.
International Search Report EP 04027314.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Olsson et al. "Radical Cystectomy in Females" Current Surgical Techniques in Urology, vol. 14, Issue 3, 2001.
Dulemba et al. "Use of a Bipolar Electrothermal Vessel Sealer in Laparoscopically Assisted Vaginal Hysterectomy" Sales Product Literature; Jan. 2004.
Johnson et al. "Evaluation of a Bipolar electrothermal Vessel Sealing Device in Hemorrhoidectomy" Sales Product Literature; Jan. 2004.
International Search Report PCT/US01/11224 dated Nov. 13, 2001.
International Search Report EP 98958575.7 dated Sep. 20, 2002.
International Search Report EP 04013772 dated Apr. 1, 2005.
International Search Report EP 05013895 dated Oct. 14, 2005.
International Search Report EP 05017281 dated Nov. 16, 2005.
Int'l Search Report EP 05013463.4 dated Sep. 28, 2005.
Int'l Search Report EP 05016399 dated Jan. 5, 2006.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 06005185.1 dated Apr. 18, 2006.
Levy et al. "Use of a New Energy-based Vessel Ligation Device During Vaginal Hysterectomy" Int'l Federation of Gynecology and Obstetrics (FIGO) World Congress; Nov. 1999.

"Innovations in Electrosurgery" Sales/Product Literature; 1999.

LigaSure Vessel Sealing System, the Seal of Confidence in General, Gynecologic, Urologic, and Laparaoscopic Surgery Sales/Product Literature; Apr. 2002.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Aug. 2003.

"Reducing Needlestick Injuries in the Operating Room" Sales/Product Literature; Mar. 2001.

Paul G. Horgan, "A Novel Technique for Parenchymal Division During Hepatectomy" The American Journal of Surgery, vol. 181, No. 3, Apr. 2001 pp. 236-237.

W. Scott Helton, "LigaSure Vessel Sealing System: Revolutionary Hemostasis Product for General Surgery" Sales/Product Literature; Oct. 1999.

Michael Choti, "Abdominoperineal Resection with the LigaSure Vessel Sealing System and LigaSure Atlas 20 cm Open Instrument" Innovations That Work, Jun. 2003.

McLeilan et al. "Vessel Sealing For Hemostasis During Gynecologic Surgery" Sales Product Literature; Nov. 1999.

Sengupta et al., "Use of a Computer-Controlled Bipolar Diathermy System in Radical Prostatectomies and Other Open Urological Surgery" ANZ Journal of Surgery (2001) 71.9 pp. 538-540.

Olssson et al. "Radical Cystectomy in Females" Current Surgical Techniques in Urology, vol. 14, Issue 3, 2001.

E. David Crawford "Use of a Novel Vessel Sealing Technology in Management of the Dorsal Veinous Complex" Sales Product Literature; Apr. 2000.

Jarrett et al., "Use of the LigaSure Vessel Sealing System for Peri-Hilar Vessels in Laparoscopic Nephrectomy" Sales Product Literature; Apr. 2000.

E. David Crawford "Evaluation of a New Vessel Sealing Device in Urologic Cancer Surgery" Sales Product Literature; Apr. 2000.

Dulemba et al. "Use of a Bipolar Electrothermal Vessel Sealer in Laparoscopically Assisted Vaginal Hysterectomy" Sales Product Literature; Jan. 2004.

Johnson et al. "Evaluation of a Bipolar electrothermal Vessel Sealing Device in Hemorrhoidectomy" Sales Product Literature; Jan. 2004.

US 6,090,109, 07/2000, Lands et al. (withdrawn)
US 6,663,629, 12/2003, Buysse et al. (withdrawn)

* cited by examiner

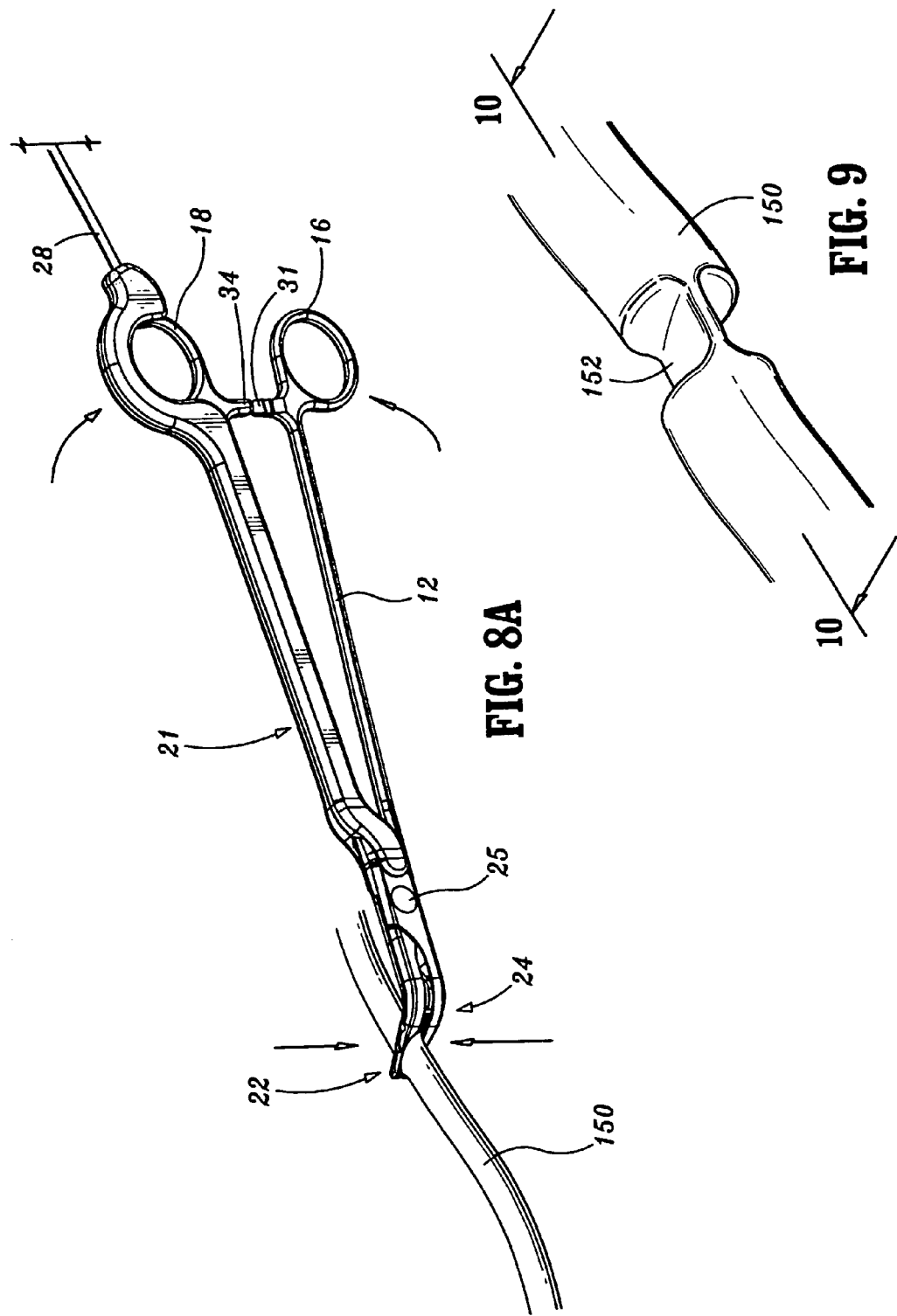

ELECTROSURGICAL INSTRUMENT WHICH REDUCES EFFECTS TO ADJACENT TISSUE STRUCTURES

CROSS REFERENCE TO RELATED APPLICATION

This application is a continuation-in-part of U.S. application Ser. No. 09/387,883, abandoned, filed on Sep. 1, 1999 which is a continuation of U.S. application Ser. No. 08/968,496, now U.S. Pat. No. 6,050,996, filed on Nov. 12, 1997 the contents of which are hereby incorporated by reference in their entirety.

BACKGROUND

The present disclosure relates to electrosurgical instruments used for open and endoscopic surgical procedures. More particularly, the present disclosure relates to a bipolar forceps having an electrode assembly which is designed to limit and/or reduce thermal spread to adjacent tissue structures and reduce the incidence of flashover during activation.

TECHNICAL FIELD

A hemostat or forceps is a simple plier-like tool which uses mechanical action between its jaws to constrict tissue and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

By utilizing an electrosurgical forceps, a surgeon can either cauterize, coagulate/desiccate tissue and/or simply reduce or slow bleeding by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is attached externally to the patient. When the electrosurgical energy is applied, the energy travels from the active electrode, to the surgical site, through the patient and to the return electrode.

Bipolar electrosurgical forceps utilize two generally opposing electrodes which are generally disposed on the inner facing or opposing surfaces of the end effectors which are, in turn, electrically coupled to an electrosurgical generator. Each electrode is charged to a different electric potential. Since tissue is a conductor of electrical energy, when the end effectors are utilized to clamp, grasp, seal and/or cut tissue therebetween, the electrical energy can be selectively transferred through the tissue.

Over the last several decades, more and more surgeons are complimenting traditional open methods of gaining access to vital organs and body cavities with endoscopes and endoscopic instruments which access organs through small puncture-like incisions. Endoscopic instruments are inserted into the patient through a cannula, or port, that has been made with a trocar. Typical sizes for cannulas range from three millimeters to twelve millimeters. Smaller cannulas are usually preferred, which, as can be appreciated, ultimately presents a design challenge to instrument manufacturers who must find ways to make surgical instruments that fit through the cannulas.

Certain surgical procedures require sealing blood vessels or vascular tissue. However, due to space limitations surgeons can have difficulty suturing vessels or performing other traditional methods of controlling bleeding, e.g., clamping and/or tying-off transected blood vessels. Blood vessels, in the range below two millimeters in diameter, can often be closed using standard electrosurgical techniques. If a larger vessel is severed, it may be necessary for the surgeon to convert the endoscopic procedure into an open-surgical procedure and thereby abandon the benefits of laparoscopy.

It is known that the process of coagulating small vessels is fundamentally different than vessel sealing. For the purposes herein the term "coagulation" is defined as a process of desiccating tissue wherein the tissue cells are ruptured and dried. The term "vessel sealing" is defined as the process of liquefying the collagen in the tissue so that the tissue cross-links and reforms into a fused mass. Thus, coagulation of small vessels is sufficient to close them, however, larger vessels need to be sealed to assure permanent closure.

Several journal articles have disclosed methods for sealing small blood vessels using electrosurgery. An article entitled *Studies on Coagulation and the Development of an Automatic Computerized Bipolar Coagulator*, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled *Automatically Controlled Bipolar Electrocoagulation—"COA-COMP"*, Neurosurg. Rev. (1984), pp. 187–190, describes a method for terminating electrosurgical power to the vessel so that charring of the vessel walls can be avoided.

With particular respect to vessel sealing, in order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important for several reasons: 1) to oppose the walls of the vessel; 2) to reduce the tissue impedance to a low enough value that allows enough electrosurgical energy through the tissue; 3) to overcome the forces of expansion during tissue heating; and 4) to contribute to the end tissue thickness which is an indication of a good seal. In some instances a fused vessel wall is optimum between 0.001 and 0.006 inches. Below this range, the seal may shred or tear and above this range the lumens may not be properly or effectively sealed.

Numerous bipolar electrosurgical instruments have been proposed in the past for various open and endoscopic surgical procedures. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, sealing and/or cutting vessels or tissue.

It has been found that using electrosurgical instruments to seal, cut and/or cauterize tissue may result in some degree of so-called "thermal spread" across adjacent tissue structure. For the purposes herein the term "thermal spread" refers generally to the heat transfer (heat conduction, heat convection or electrical current dissipation) traveling along the periphery of the electrically conductive surfaces. This can also be termed "collateral damage" to adjacent tissue. As can be appreciated, reducing the thermal spread during an electrical procedure reduces the likelihood of unintentional or undesirable collateral damage to surrounding tissue structures which are adjacent to an intended treatment site.

Instruments which include dielectric coatings disposed along the outer surfaces are known and are used to prevent tissue "blanching" at points normal to the activation site. In other words, these coatings are primarily designed to reduce accidental burning of tissue as a result of incidental contact with the outer surfaces end effectors. So far as is known these coating are not designed or intended to reduce collateral tissue damage or thermal spread to adjacent tissue (tissue lying along the tissue plane).

It has also been found that cleaning and sterilizing many of the prior art bipolar instruments is often impractical as electrodes and/or insulation can be damaged. More particularly, it is known that electrically insulative materials, such as plastics, can be damaged or compromised by repeated sterilization cycles which may ultimately effect the reliability of the instrument and cause so-called "flashover." Flashover as used herein relates to a visual anomaly which develops as a result of inconsistent current tracking over the surface of the insulator or insulative coating and/or activation irregularities which may occur when the instrument is repeatedly used during surgery. Put simply, flashover tends to char the surface of the insulate and may effect the life of the instrument and/or the electrode assembly. The effects and industry standards with respect to flashover are discussed in detail in the *Annual Book of ASTM Standards*, Vol. 10.02, Designations: D495-84; D618; D2303; and D3638.

Several electrosurgical instruments have been introduced which are known to solve many of the aforementioned problems associated with sealing, cutting, cauterizing and/or coagulating differently-sized vessels. Some of these instruments are described in co-pending U.S. patent application Ser. No. 09/178,027 filed on Oct. 23, 1998, entitled OPEN VESSEL SEALING FORCEPS WITH DISPOSABLE ELECTRODES, co-pending U.S. patent application Ser. No. 09/425,696 filed on Oct. 22, 1999, entitled OPEN VESSEL SEALING FORCEPS WITH DISPOSABLE ELECTRODES, co-pending U.S. patent application Ser. No. 09/177,950 filed on Oct. 23, 1998, entitled ENDOSCOPIC BIPOLAR ELECTROSURGICAL FORCEPS; and co-pending U.S. patent application Ser. No. 09/621,029 filed on Jul. 21, 2000, entitled ENDOSCOPIC BIPOLAR ELECTROSURGICAL FORCEPS, the entire contents of all of which are hereby incorporated by reference herein.

Thus, a need exists to develop an electrosurgical instrument which can effectively reduce the undesirable effects of thermal spread across tissue structures and effectively reduce the incidence of flashover.

SUMMARY

The present disclosure generally relates to an open and/or endoscopic electrosurgical instrument which includes electrodes which are electrically and thermally isolated from the remainder of the instrument by a uniquely designed insulating substrate and electrically conductive surface. It is envisioned that the geometric shape of the insulating substrate relative to the geometric shape of the conductive surface contributes to the overall reduction of collateral damage to adjacent tissue structures. The uniquely-designed geometric configuration of the insulating substrate in connection with the chemical characteristics of the insulating substrate also contributes to a reduction in the incidence of flashover.

More particularly, the present disclosure relates to an electrosurgical instrument which includes opposing end effectors and a handle for effecting movement of the end effectors relative to one another. The instrument includes a housing and a pair of electrodes. Each electrode preferably includes an electrically conductive surface (e.g., which can be dimensioned for sealing, clamping and/or cutting) and an insulating substrate which is dimensioned to be selectively engageable with the end effectors such that the electrodes reside in opposing relation relative to one another. The dimensions of the insulating substrate are different from the dimensions of the electrically conductive surface to reduce thermal spread to adjacent tissue structures. The insulating substrate is made from a material having a Comparative Tracking Index of about 300 volts to about 600 volts to reduce the incidence of flashover Preferably, the dimensions of the insulating substrate are different from the dimensions of the electrically conductive surface which not only reduces thermal spread to adjacent tissue structures but may contribute to a reduction in the incidence of flashover.

In other embodiments, the insulating substrate is mounted to the electrically conductive surface by stamping, by overmolding, by overmolding a stamped plate and/or by overmolding a metal injection molded plate. All of these manufacturing techniques produce an electrode having an electrically conductive surface which is substantially surrounded by an insulating substrate. These uniquely described embodiments described herein are contemplated to effectively reduce the thermal spread to adjacent tissue structures during and/or immediately following activation. Moreover, certain cross section deviations may also contribute to a reduction in the incidence of flashover. The electrically conductive surface may also include a pinch trim which facilitates secure engagement of the electrically conductive surface to the insulating substrate and also simplifies the overall manufacturing process.

In another embodiment, the electrically conductive surface includes an outer peripheral edge which has a radius and the insulator meets the electrically conductive surface along an adjoining edge which is generally tangential to the radius and/or meets along the radius. Preferably, at the interface, the electrically conductive surface is raised relative to the insulator.

The insulating substrate may be made from a plastic or plastic-based material having a Comparative Tracking Index of about 300 volts to about 600 volts. Preferably, the insulating substrate is substrate is made from a group of materials which include Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate. Alternatively, a non-plastic insulating material, e.g., ceramic, may be used in lieu of or in combination with one or more of the above-identified materials to facilitate the manufacturing process and possibly contribute to the overall reduction of thermal spread to adjacent tissue structures In another embodiment of the present disclosure, the insulating substrate of each electrode includes at least one mechanical interface for engaging a complimentary mechanical interface disposed on the corresponding end effector of the instrument. Preferably, the mechanical interface of the substrate includes a detent and the mechanical interface of the corresponding end effector includes a complimentary socket for receiving the detent.

Other embodiments of the present disclosure include a housing having a bifurcated distal end which forms two resilient and flexible prongs which each carry an electrode designed to engage a corresponding end effector. In another embodiment, the end effectors are disposed at an angle (α) relative to the distal end of the shaft of the electrosurgical instrument. Preferably, the angle is about sixty degrees to about seventy degrees. The end effectors and, in turn, the electrodes, can also be dimensioned to include a taper along a width "W" (See FIG. 2).

The present disclosure also relates to an electrosurgical instrument having a handle and at least one shaft for effecting movement of a pair of opposing end effectors relative to one another. An electrode assembly engages the shaft and includes a pair of electrodes. Each electrode is removably engageable with a corresponding end effector and includes an electrically conductive surface with a first geometric shape and an insulating substrate with a second geometric shape. Preferably, the second geometric shape of the insulating substrate is different from the first geometric shape of the conductive surface which effectively reduces thermal spread to adjacent tissue structures and may also contribute to a reduction in the incidence of flashover.

In one embodiment, the electrode assembly which engages the instrument is removable, disposable and replaceable after the electrode assembly is used beyond its intended number of activation cycles. Alternatively, the electrode assembly and/or the electrodes may be integrally associated with the end effectors of the instrument and are not removable. In this instance, the electrosurgical instrument (open or endoscopic) may be designed for single use applications and the entire instrument is fully disposable after the surgery is completed.

BRIEF DESCRIPTION OF THE DRAWINGS

FIG. 8A is a perspective view of the open forceps of the present disclosure showing the operative motion of the electrosurgical instrument about a tubular vessel;

FIG. 9 is an enlarged, partial perspective view of a sealing site of a tubular vessel;

DETAILED DESCRIPTION

It has been found that by altering the configuration of the electrode insulating material relative to the electrically conductive surface, surgeons can more readily, more easily and more effectively reduce thermal spread across or to adjacent tissue and/or reduce the incidence of flashover. For the purposes herein the term "thermal spread" refers generally to the heat transfer (heat conduction, heat convection or electrical current dissipation) dissipating along the periphery of the electrically conductive or electrically active surfaces to adjacent tissue. This can also be termed "collateral damage" to adjacent tissue. The term "flashover" is simply a visual anomaly which occurs during activation as a result of inconsistent and/or irregular current tracking over the surface of the insulate which may occur when the instrument is repeatably used during surgery. Flashover tends to char the surface of the insulate and may effect the life of the instrument.

It is envisioned that the configuration of the insulating material which surrounds the perimeter of the electrically conductive surface will effectively reduce current and thermal dissipation to adjacent tissue areas and generally restrict current travel to areas between the opposing electrodes. As mentioned above, this is different from dielectrically coating the outer surfaces of the instrument to prevent tissue "blanching" at points normal to the intended site. These coatings are not designed or intended to reduce collateral tissue damage or thermal spread to adjacent tissue (tissue lying along the tissue activation plane).

More particularly, it is contemplated that altering the geometrical dimensions of the insulator relative to the electrically conductive surface alters the electrical path thereby influencing the thermal spread/collateral damage to adjacent tissue structures. Preferably, the geometry of the insulating substrate also isolates the two electrically opposing poles (i.e., electrodes) from one another thereby reducing the possibility that tissue or tissue fluids can create an unintended bridge or path for current travel. In other words, the insulator and electrically conductive surface are preferably dimensioned such that the current is concentrated between the opposing electrically conductive surfaces as explained in more detail below.

It is also contemplated that one way to reduce the incidence of flashover is to alter the geometry of the insulation relative to the electrically conductive surface which effectively increases the overall distance that the electrical current must travel along the predetermined electrical path. It is also envisioned that manufacturing the insulating substrate from a specific material having certain properties will, likewise, reduce the incidence of flashover during activation.

Figure 1:
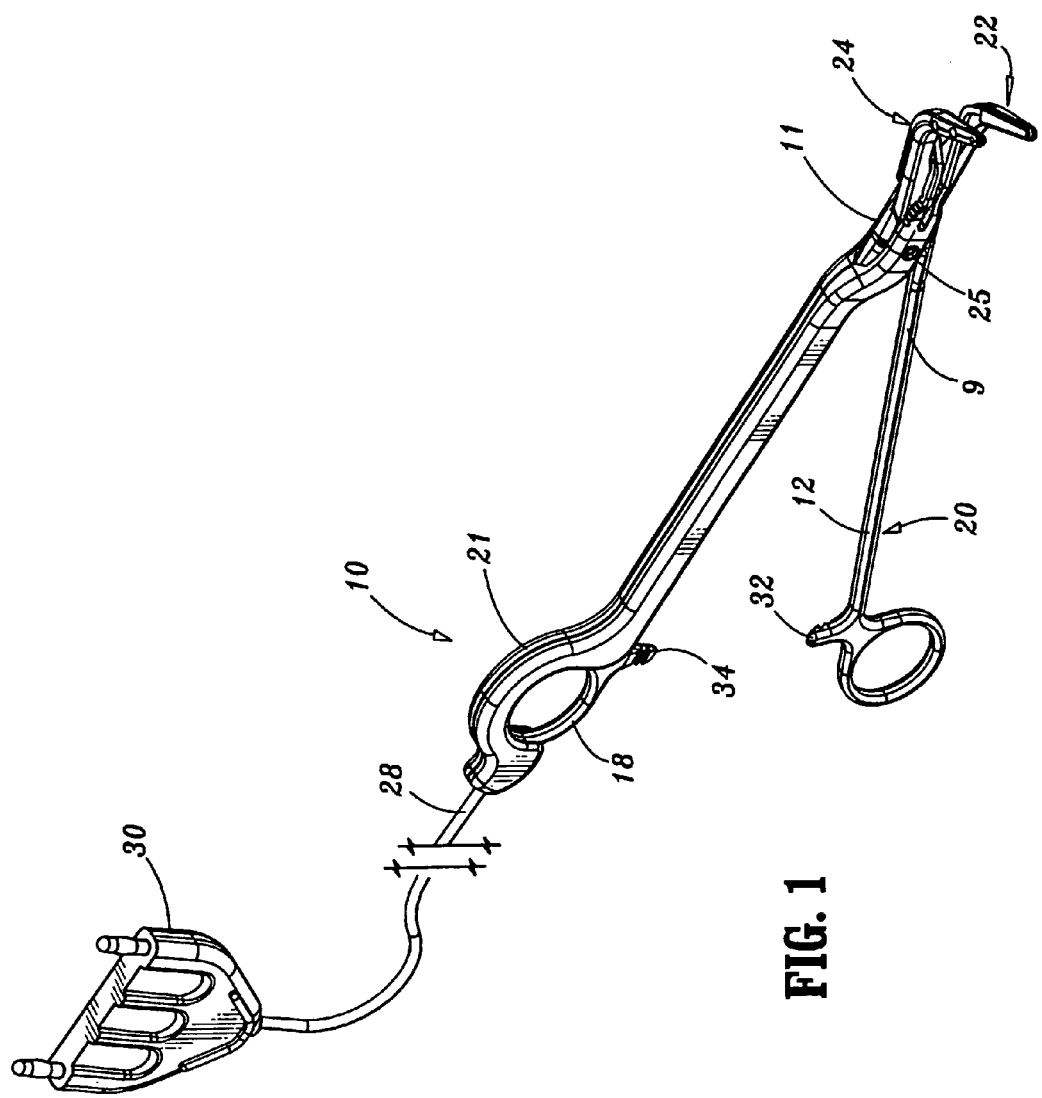
FIG. 1 is a perspective view of an open electrosurgical instrument according to one embodiment of the present disclosure.
Figure 2:
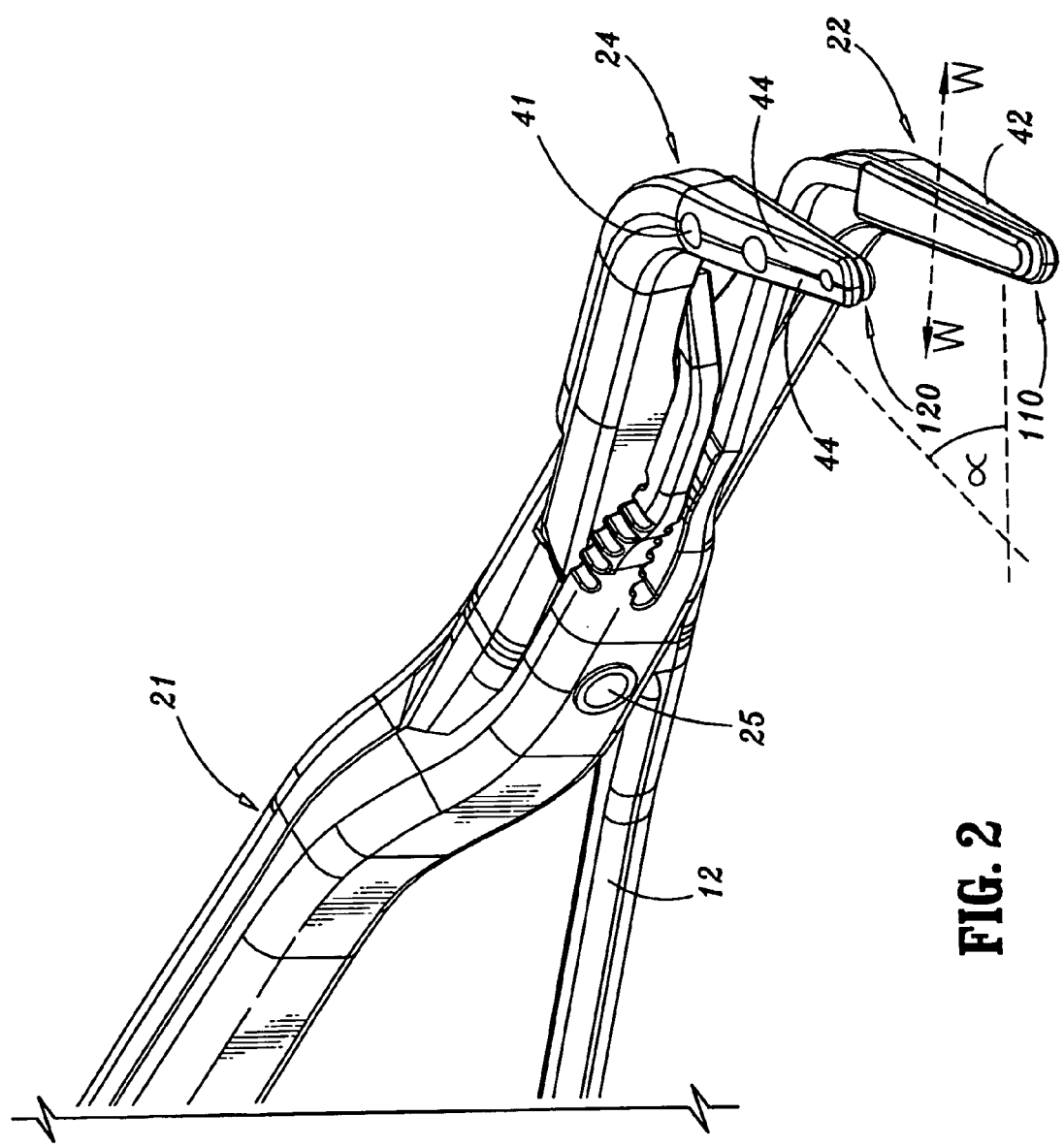
FIG. 2 is an enlarged, perspective view of a distal end of the electrosurgical instrument shown in FIG. 1.
Figure 3:
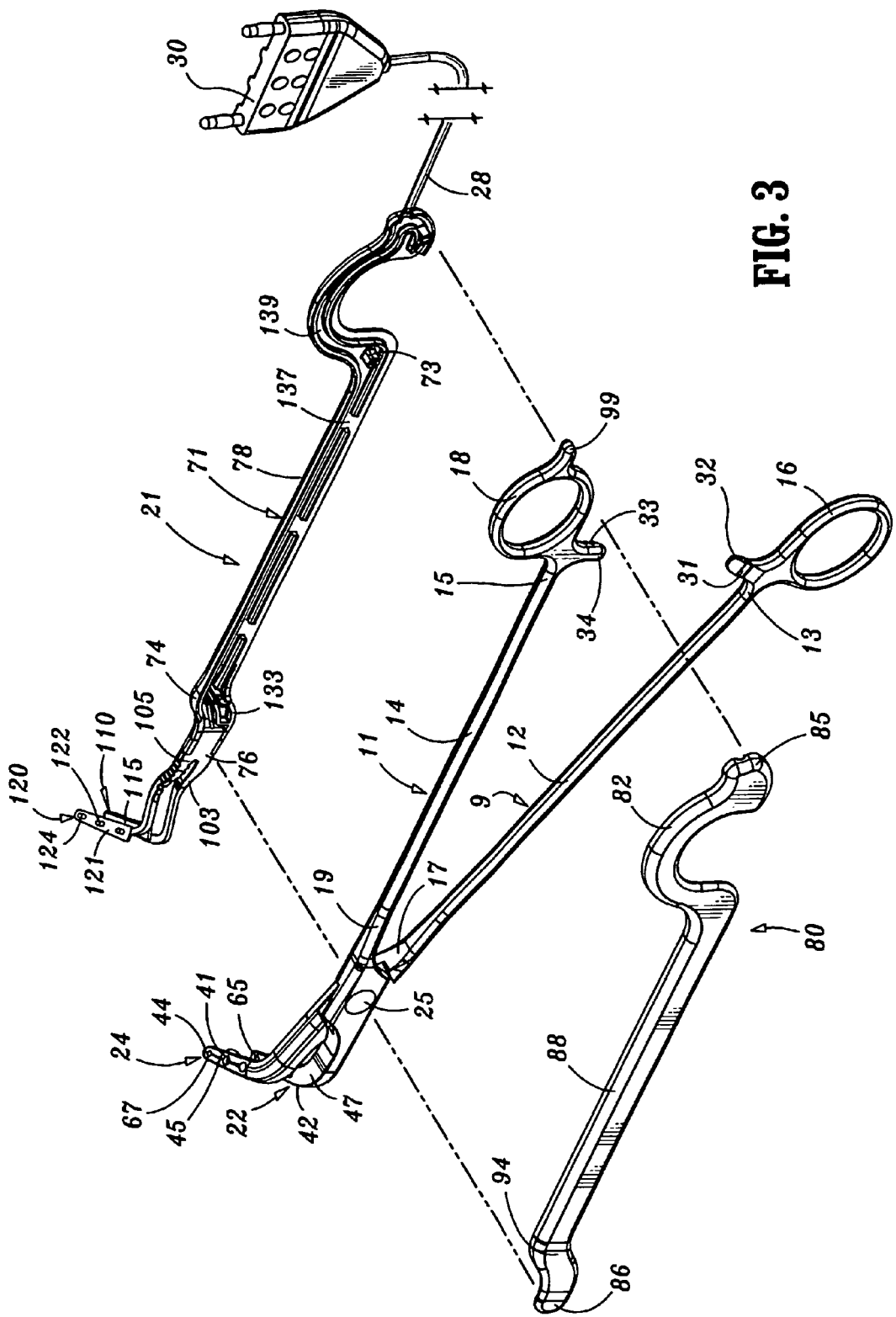
FIG. 3 is a perspective view with parts separated of the electrosurgical instrument shown in FIG. 1.

Referring now to FIGS. 1–3, a bipolar forceps 10 for use with open surgical procedures is shown by way of example and includes a mechanical forceps 20 and an electrode assembly 21. In the drawings and in the description which follows, the term "proximal", as is traditional, will refer to the end of the forceps 10 which is closer to the user, while the term "distal" will refer to the end which is further from the user. In addition, although the majority of the figures, i.e., FIGS. 1–7A and 8A, show one embodiment of the presently described instrument for use with open surgical procedures, e.g., forceps 20, it is envisioned that the same properties as shown and described herein may also be employed with or incorporated on an endoscopic instrument 100 such as the embodiment shown by way of example in FIG. 8B.

FIGS. 1–3 show mechanical forceps 20 which includes first and second members 9 and 11 which each have an elongated shaft 12 and 14, respectively. Shafts 12 and 14 each include a proximal end 13 and 15 and a distal end 17 and 19, respectively. Each proximal end 13, 15 of each shaft portion 12, 14 includes a handle member 16 and 18 attached thereto which allows a user to effect movement of at least one of the shaft portions, e.g., 12 relative to the other, e.g. 14. Extending from the distal ends 17 and 19 of each shaft portion 12 and 14 are end effectors 24 and 22, respectively. The end effectors 22 and 24 are movable relative to one another in response to movement of handle members 16 and 18.

Preferably, shaft portions 12 and 14 are affixed to one another at a point proximate the end effectors 24 and 22 about a pivot 25 such that movement of one of the handles 16, 18 will impart relative movement of the end effectors 24 and 22 from an open position wherein the end effectors 22 and 24 are disposed in spaced relation relative to one another to a closed position wherein the end effectors 22 and 24 incorporate a tubular vessel 150 therebetween (see FIGS. 8A and 8B) to effect sealing, cutting or grasping. It is envisioned that pivot 25 has a large surface area to resist twisting and movement of forceps 10 during activation. It is also envisioned that the forceps 10 can be designed such that movement of one or both of the handles 16 and 18 will only cause one of the end effectors, e.g., 24, to move with respect to the other end effector, e.g., 22.

As best seen in FIG. 3, end effector 24 includes an upper or first jaw member 44 which has an inner facing surface 45 and a plurality of mechanical interfaces disposed thereon which are dimensioned to releasable engage a portion of the electrode assembly 21 which will be described in greater detail below. Preferably, the mechanical interfaces include sockets 41 which are disposed at least partially through inner facing surface 45 of jaw member 44 and which are dimensioned to receive a complimentary detent 122 attached to upper electrode 120 of the disposable electrode assembly 21. While the term "socket" is used herein, it is contemplated that either a male or female mechanical interface may be used on jaw member 44 with a mating mechanical interface disposed on the electrode assembly 21.

In some cases, it may be preferable to manufacture mechanical interfaces 41 along another side of jaw member 44 to engage a complimentary mechanical interface of the electrode assembly 21 in a different manner, e.g., from the side. Jaw member 44 also includes an aperture 67 disposed at least partially through inner face 45 of end effector 24 which is dimensioned to receive a complimentary guide pin 124 disposed on electrode 120 of the electrode assembly 21.

End effector 22 includes a second or lower jaw member 42 which has an inner facing surface 47 which opposes inner facing surface 45. Preferably, jaw members 42 and 44 are dimensioned generally symmetrically, however, in some cases it may be preferable to manufacture the two jaw members 42 and 44 asymmetrically depending upon a particular purpose. In much the same fashion as described above with respect to jaw member 44, jaw member 42 also includes a plurality of mechanical interfaces or sockets 43 disposed thereon which are dimensioned to releasable engage a complimentary portion 112 disposed on electrode 110 of the electrode assembly 21 as described below. Likewise, jaw member 42 also includes an aperture 65 disposed at least partially through inner face 47 which is dimensioned to receive a complimentary guide pin 127 (see FIG. 4) disposed on electrode 110 of the electrode assembly 21.

Preferably, the end effectors 22, 24 (and, in turn, the jaw members 42 and 44 and the corresponding electrodes 110 and 120) are disposed at an angle alpha ($\alpha$) relative to the distal ends 19, 17 (See FIG. 2). It is contemplated that the angle alpha ($\alpha$) is in the range of about 50 degrees to about 70 degrees relative to the distal ends 19, 17. It is envisioned that angling the end effectors 22, 24 at an angle alpha ($\alpha$) relative to the distal ends 19, 17 may be advantageous for two reasons: 1) the angle of the end effectors, jaw members and electrodes will apply more constant pressure for cutting and/or for a constant tissue thickness at parallel for sealing purposes; and 2) the thicker proximal portion of the electrode, e.g., 110, (as a result of the taper along width "W") will resist bending due to the reaction force of the tissue 150. The tapered "W" shape (FIG. 2) of the electrode 110 is determined by calculating the mechanical advantage variation from the distal to proximal end of the electrode 110 and adjusting the width of the electrode 110 accordingly. It is contemplated that dimensioning the end effectors 22, 24 at an angle of about 50 degrees to about 70 degrees is preferred for accessing and activating specific anatomical structures relevant to prostatectomies and cystectomies, e.g., the dorsal vein complex and the lateral pedicles.

Preferably, shaft members 12 and 14 of the mechanical forceps 20 are designed to transmit a particular desired force to the opposing inner facing surfaces of the of the jaw members 22 and 24, respectively, when clamped or during sealing and/or cutting. In particular, since the shaft members 12 and 14 effectively act together in a spring-like manner (i.e., bending that behaves like a spring), the length, width, height and deflection of the shaft members 12 and 14 will directly effect the overall transmitted force imposed on opposing jaw members 42 and 44. Preferably, jaw members 22 and 24 are more rigid than the shaft members 12 and 14 and the strain energy stored in the shaft members 12 and 14 provides a constant closure force between the jaw members 42 and 44.

Each shaft member 12 and 14 also includes a ratchet portion 32 and 34, respectively. Preferably, each ratchet, e.g., 32, extends from the proximal end 13 of its respective shaft member 12 towards the other ratchet 34 in a generally vertically aligned manner such that the inner facing surfaces of each ratchet 32 and 34 abut one another when the end effectors 22 and 24 are moved from the open position to the closed position. Each ratchet 32 and 34 includes a plurality of flanges 31 and 33, respectively, which project from the inner facing surface of each ratchet 32 and 34 such that the ratchets 32 and 34 can interlock in at least one position. In the embodiment shown in FIG. 1, the ratchets 32 and 34 interlock at several different positions. Preferably, each ratchet position holds a specific, i.e., constant, strain energy in the shaft members 12 and 14 which, in turn, transmits a specific force to the end effectors 22 and 24 and, thus, the electrodes 120 and 110. This is particularly relevant during sealing.

In some cases it may be preferable to include other mechanisms to control and/or limit the movement of the jaw members 42 and 44 relative to one another. For example, a ratchet and pawl system could be utilized to segment the movement of the two handles into discrete units which will, in turn, impart discrete movement to the jaw members 42 and 44 relative to one another.

Preferably, at least one of the shaft members, e.g., 14, includes a tang 99 which facilitates manipulation of the forceps 20 during surgical conditions as well as facilitates attachment of electrode assembly 21 on mechanical forceps 20 as will be described in greater detail below.

Figure 5:
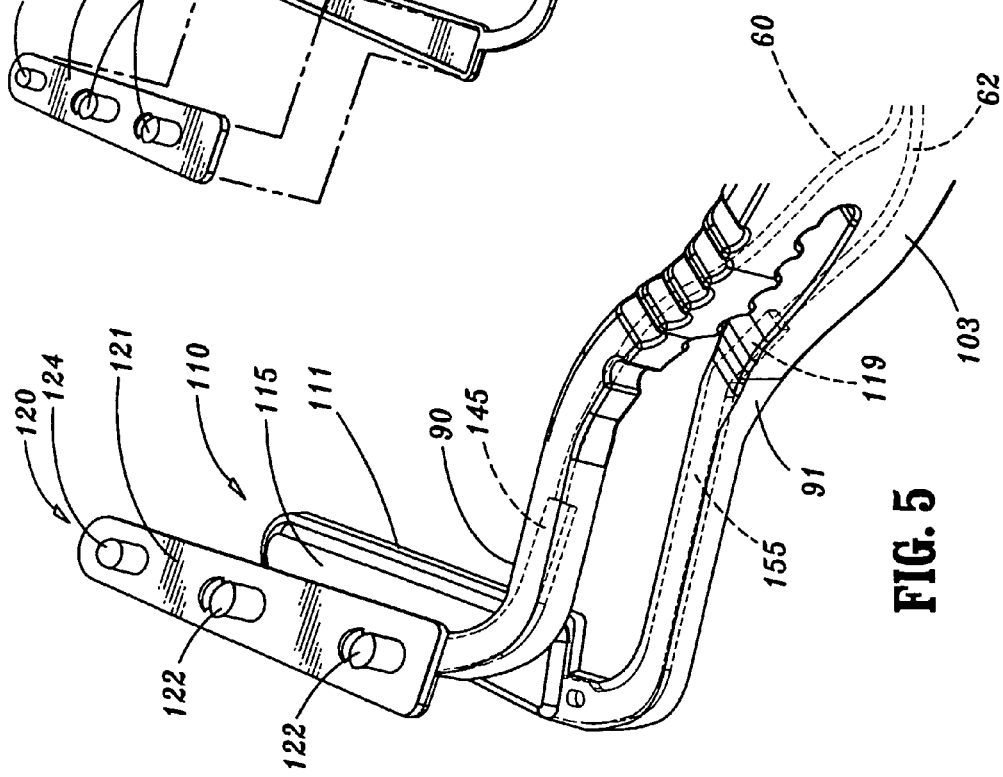
FIG. 5 is an enlarged, perspective view of a distal end of the electrode assembly of FIG. 4.

As best seen in FIGS. 2, 3 and 5, one embodiment of the electrosurgical instrument includes electrode assembly 21 is designed to work in combination with mechanical forceps 20. Preferably, electrode assembly 21 includes housing 71 which has a proximal end 77, a distal end 76 and an elongated shaft plate 78 disposed therebetween. A handle plate 72 is disposed near the proximal end 77 of housing 71 and is sufficiently dimensioned to releasably engage and/or encompass handle 18 of mechanical forceps 20. Likewise, shaft plate 78 is dimensioned to encompass and/or releasably engage shaft 14 and pivot plate 74 disposed near the distal end 76 of housing 71 and is dimensioned to encompass pivot 25 and at least a portion of distal end 19 of mechanical forceps 20. It is contemplated that the electrode assembly 21 can be manufactured to engage either the first or second members 9 and 11 of the mechanical forceps 20 and its respective component parts 12, 16 or 14, 18, respectively.

In the embodiment shown in FIG. 3, handle 18, shaft 14, pivot 25 and a portion of distal end 19 are all dimensioned to fit into corresponding channels located in housing 71. For example, a channel 139 is dimensioned to receive handle 18, a channel 137 is dimensioned to receive shaft 14 and a channel 133 is dimensioned to receive pivot 25 and a portion of distal end 19.

Electrode assembly 21 may also includes a cover plate 80 which is designed to encompass and/or engage mechanical forceps 20 in a similar manner as described with respect to the housing 71. More particularly, cover plate 80 includes a proximal end 85, a distal end 86 and an elongated shaft plate 88 disposed therebetween. A handle plate 82 is disposed near the proximal end 85 and is preferably dimensioned to releasable engage and/or encompass handle 18 of mechanical forceps 20. Likewise, shaft plate 88 is dimensioned to encompass and/or releasable engage shaft 14 and a pivot plate 94 disposed near distal end 86 is designed to encompass pivot 25 and distal end 19 of mechanical forceps 20. Preferably, handle 18, shaft 14, pivot 25 and distal end 19 are all dimensioned to fit into corresponding channels (not shown) located in cover plate 80 in a similar manner as described above with respect to the housing 71.

Figure 4:
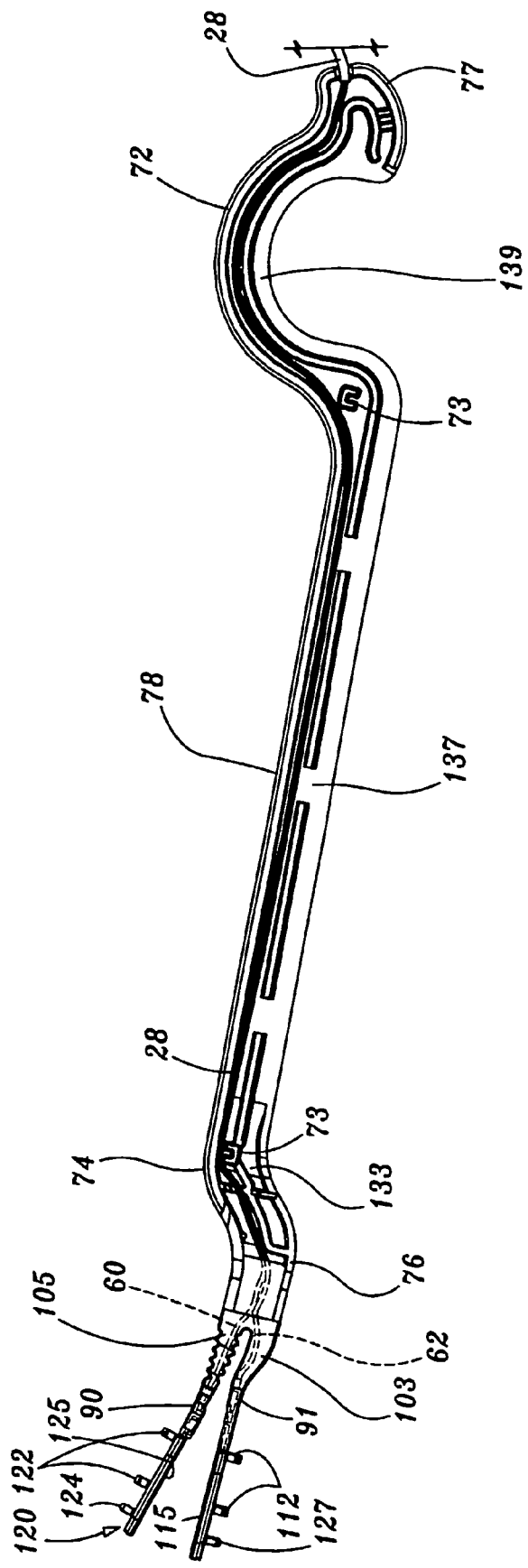
FIG. 4 is an enlarged, side view of an electrode assembly of FIG. 1 shown without a cover plate.
Figure 7A:
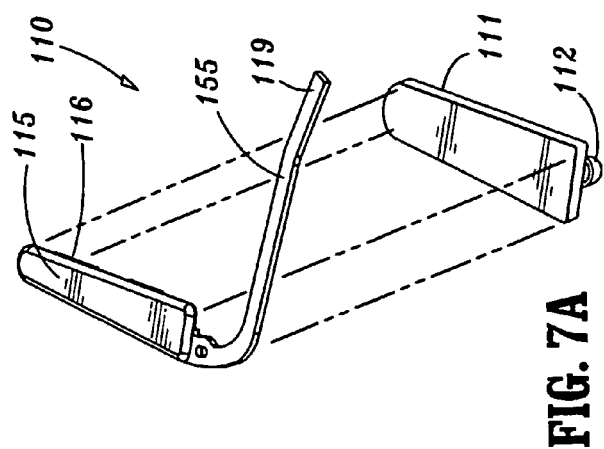
FIG. 7A is a perspective view with parts separated of a lower electrode of the electrode assembly of FIG. 5.

As best seen with respect to FIGS. 3 and 4, housing 71 and cover plate 80 are designed to engage one another over first member, e.g., 11, of mechanical forceps 20 such that first member 11 and its respective component parts, e.g., handle 18, shaft 14, distal end 19 and pivot 25, are disposed therebetween. Preferably, housing 71 and cover plate 80 include a plurality of mechanical interfaces disposed at various positions along the interior of housing 71 and cover plate 80 to effect mechanical engagement with one another. More particularly, a plurality of sockets 73 are disposed proximate handle plate 72, shaft plate 78 and pivot plate 74 of housing 71 and are dimensioned to releasably engage a corresponding plurality of detents (not shown) extending from cover plate 80. It is envisioned that either male or female mechanical interfaces or a combination of mechanical interfaces may be disposed within housing 71 with mating mechanical interfaces disposed on or within cover plate 80.

As best seen with respect to FIGS. 5–7A, the distal end 76 of electrode assembly 21 is bifurcated such that two pronglike members 103 and 105 extend outwardly therefrom to support electrodes 110 and 120, respectively. More particularly, electrode 120 is affixed at an end 90 of prong 105 and electrode 110 is affixed at an end 91 of prong 103. It is envisioned that the electrodes 110 and 120 can be affixed to the ends 91 and 90 in any known manner, e.g., friction-fit, slide-fit, snap-fit engagement, crimping, etc. Moreover, it is contemplated that the electrodes 110 and 120 may be selectively removable from ends 90 and 91 depending upon a particular purpose and/or to facilitate assembly of the electrode assembly 21. As mentioned above, the inventive concepts disclosed herein may also relate to an electrosurgical instrument which does not include a selectively detachable electrode assembly, but, rather, includes end effectors which have integrally associated electrodes disposed thereon.

A pair of wires 60 and 62 are connected to the electrodes 120 and 110, respectively, as best seen in FIGS. 4 and 5. Preferably, wires 60 and 62 are bundled together and form a wire bundle 28 (FIG. 4) which runs from a terminal connector 30 (see FIG. 3), to the proximal end 77 of housing 71, along the interior of housing 71, to distal end 76. Wire bundle 28 is separated into wires 60 and 62 proximate distal end 76 and the wires 60 and 62 are connected to each electrode 120 and 110, respectively. In some cases it may be preferable to capture the wires 60 and 62 or the wire bundle 28 at various pinch points along the inner cavity of the electrode assembly 21 and enclose the wires 60 and 62 within electrode assembly 21 by attaching the cover plate 80.

This arrangement of wires 60 and 62 is designed to be convenient to the user so that there is little interference with the manipulation of bipolar forceps 10. As mentioned above, the proximal end of the wire bundle 28 is connected to a terminal connector 30, however, in some cases it may be preferable to extend wires 60 and 62 to an electrosurgical generator (not shown).

Figure 6:
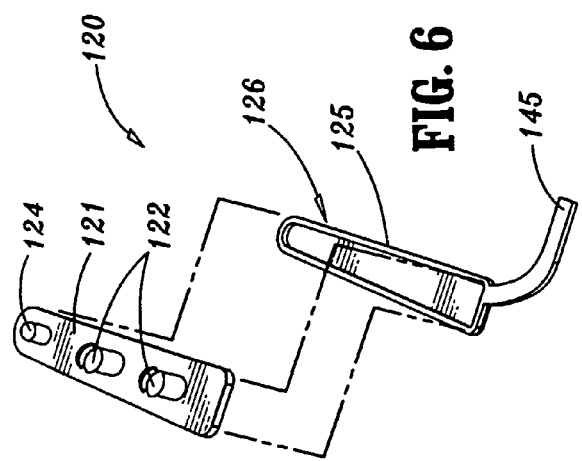
FIG. 6 is a perspective view with parts separated of an upper electrode of the electrode assembly of FIG. 5.
Figure 7B:
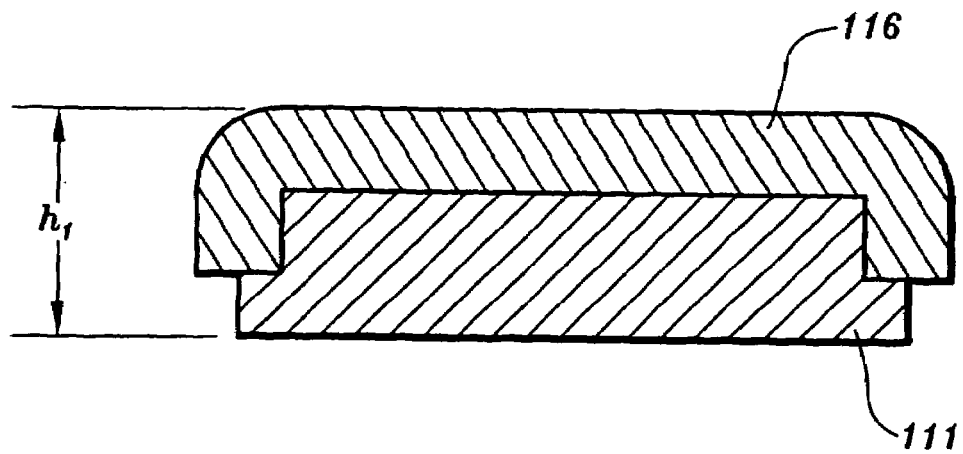
FIG. 7B is a cross section of a prior art electrode configuration with the electrode extending over the sides of the insulator.
Figure 7C:
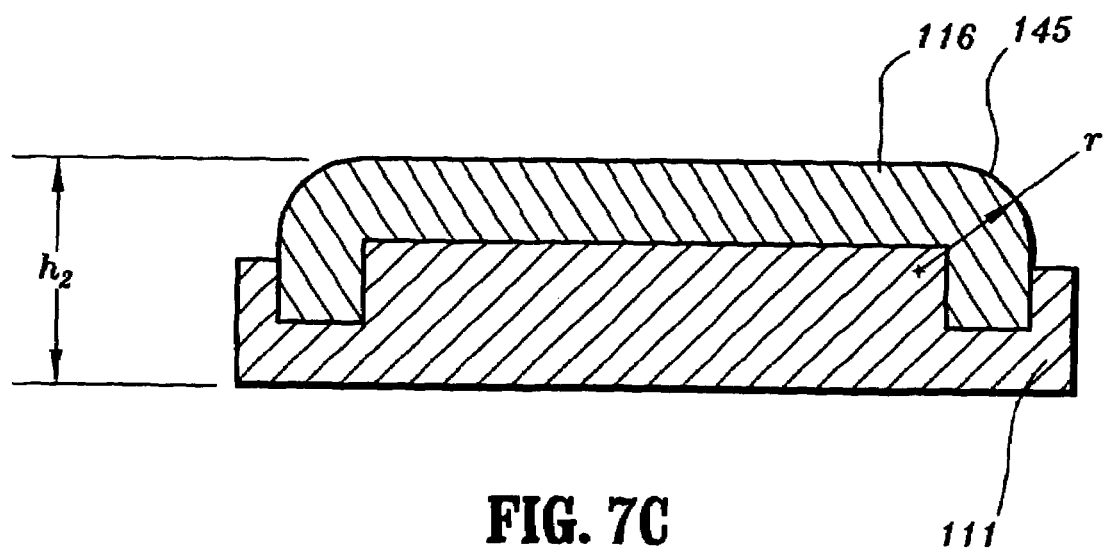
FIG. 7C is a cross section of an electrode with the insulator extending beyond the sides of a radiused electrode.

As best seen in FIG. 6, electrode 120 includes an electrically conductive surface 126 and an electrically insulative substrate 121 which are attached to one another by snap-fit engagement or some other method of assembly, e.g., slide-fit, overmolding of a stamping or metal injection molding. Preferably, substrate 121 is made from molded plastic material and is shaped to mechanically engage a corresponding socket 41 located in jaw member 44 of end effector 24 (see FIG. 2). The substrate 121 not only insulates the electric current but it also aligns electrode 120 both of which contribute to the reduction of thermal spread across the tissue and a reduction of the incidence of flashover. Moreover, by attaching the conductive surface 126 to the substrate 121 utilizing one of the above assembly techniques, the alignment and thickness, i.e., height "h2", of the electrode 120 can be controlled. For example and as best illustrated in the comparison of FIGS. 7B and 7C, the overmolding manufacturing technique reduces the overall height "h2" (FIG. 7C) of the electrode 120 compared to traditional manufacturing techniques which yield a height of "h1" (FIG. 7B). The smaller height "h2" allows a user access to smaller areas within the body and facilitates activation around more delicate tissue areas.

Moreover, it is contemplated that the overmolding technique provides more insulation along the side of the electrically conductive surface which also reduces thermal spread due to less electrode to tissue contact. It is envisioned that by dimensioning substrate, e.g., 121 and electrode 120 in this fashion (i.e., with reduced conductive surface area), the current is restricted (i.e., concentrated) to the intended area rather than current traveling to tissue outside the intended area which may come into contact with an outer edge of the electrode 120 (see FIG. 7B).

Providing more insulation along the side of the electrically conductive surface may also effectively reduce the incidence of flashover.

Preferably, substrate 121 includes a plurality of bifurcated detents 122 which are shaped to compress during insertion into sockets 41 and expand and releasably engage sockets 41 after insertion. It is envisioned that snap-fit engagement of the electrode 120 and the jaw member 44 will accommodate a broader range of manufacturing tolerances. Substrate 121 also includes an alignment or guide pin 124 which is dimensioned to engage aperture 67 of jaw member 44.

A slide-fit technique is also contemplated such as the slide-fit technique described with respect to commonly-assigned, co-pending U.S. application Ser. No. 10/474,227, by Tetzlaff et al., the entire contents of which is hereby incorporated by reference herein.

Conductive surface 126 includes a wire crimp 145 designed to engage the distal end 90 of prong 105 of electrode assembly 21 and electrically engage a corresponding wire connector affixed to wire 60 located within electrode assembly 21. Conductive surface 126 also includes an opposing face 125 which is designed to conduct an electrosurgical current to a tubular vessel or tissue 150 when it is held thereagainst. It is envisioned that the conductive surfaces 126 (116) may be dimensioned as a sealing surface, a clamping surface and/or a shearing or cutting surface depending upon a particular purpose.

Electrode 110 includes similar elements and materials for insulating and conducting electrosurgical current to tissue 150. More particularly, electrode 110 includes an electrically conductive surface 116 and an electrically insulative substrate 111 which are attached to one another by one of the above methods of assembly. Substrate 111 includes a plurality of detents 112 which are dimensioned to engage a corresponding plurality of sockets 43 and aperture 65 located in jaw member 42. Conductive surface 116 includes an extension 155 having a wire crimp 119 which engages the distal end 91 of prong 103 and electrically engages a corresponding wire connector affixed to wire 62 located in housing 71. Conductive surface 116 also includes an opposing face 115 which conducts an electrosurgical current to a tubular vessel or tissue 150 when it is held thereagainst. It is contemplated that electrodes 110 and 120 can be formed as one piece and include similar components and/or dimensions for insulating and conducting electrical energy in a manner to effectively reduce thermal spread and the incidence of flashover. Stray current may be further restricted by casting the forceps and/or manufacturing the forceps using a non-conductive material and/or coating the edges of the electrodes 110 and 120 with an insulative coating.

As mentioned above, it is envisioned that flashover and thermal spread may be reduced by altering the physical dimensions (geometry/shape) of the insulators and/or the chemical characteristics of the insulators. With particular respect to thermal spread, it is envisioned that manufacturing the electrodes 110 and 120 in this fashion will reduce thermal spread and stray currents that may travel to the electrosurgical instrument. More particularly, the varying geometry of the insulator 111 compared to the electrically conductive surface 116 also isolates the two opposing poles during activation thereby reducing the possibility that tissue or fluids will bridge a path for stray current travel to surrounding tissue.

With respect to flashover, altering the geometry of the insulator 111 and/or electrically conductive surface 116 creates a longer path for the current to travel over the insulator 111 before flashover occurs.

For example and as best shown in the comparison of FIG. 7B (prior art) with newly disclosed FIGS. 7C, 7D, 14A and 14B substrates 111, 121 are designed to extend along width "W" (FIG. 2) such that the width of the insulating substrate, e.g., 111, exceeds the width of the electrically conductive surface, e.g., 116. It is envisioned that these electrically conductive surface 116 and insulator 111 configurations may be accomplished by various manufacturing techniques such as overmolding of a stamping and/or metal injection molding. Stamping is defined herein to encompass virtually any press operation known in the trade, including, but not limited to: blanking, shearing, hot or cold forming, drawing, bending and coining. Other manufacturing techniques may also be employed to achieve similar electrically conductive surface 116 and insulator 111 configurations which will effectively reduce thermal spread to adjacent tissue.

Figure 7D:
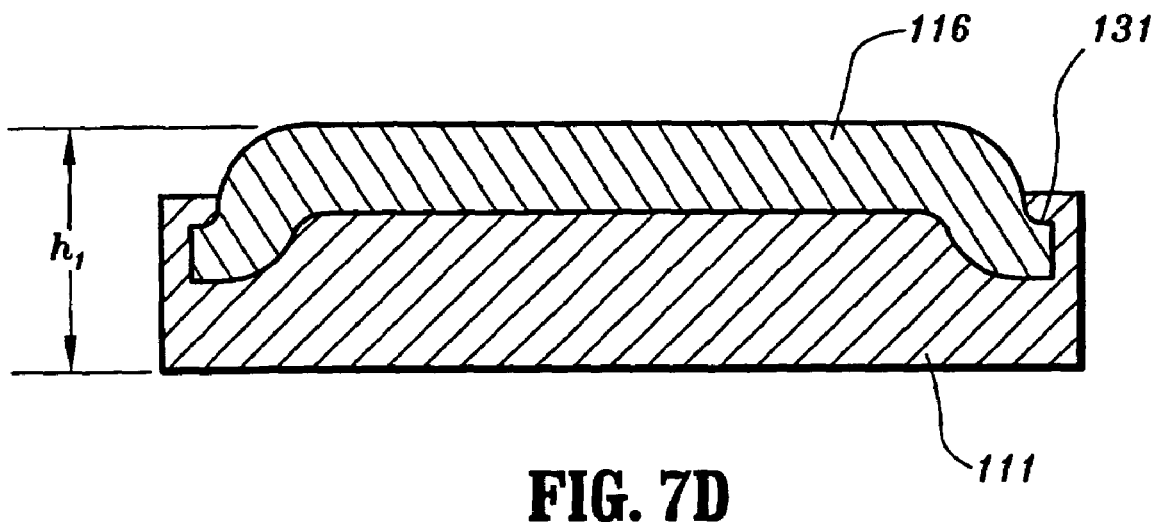
FIG. 7D is a cross section of an overmolded stamped electrode configuration showing the insulator capturing a pinch trim which depends from the electrically conductive surface.
Figure 7E:
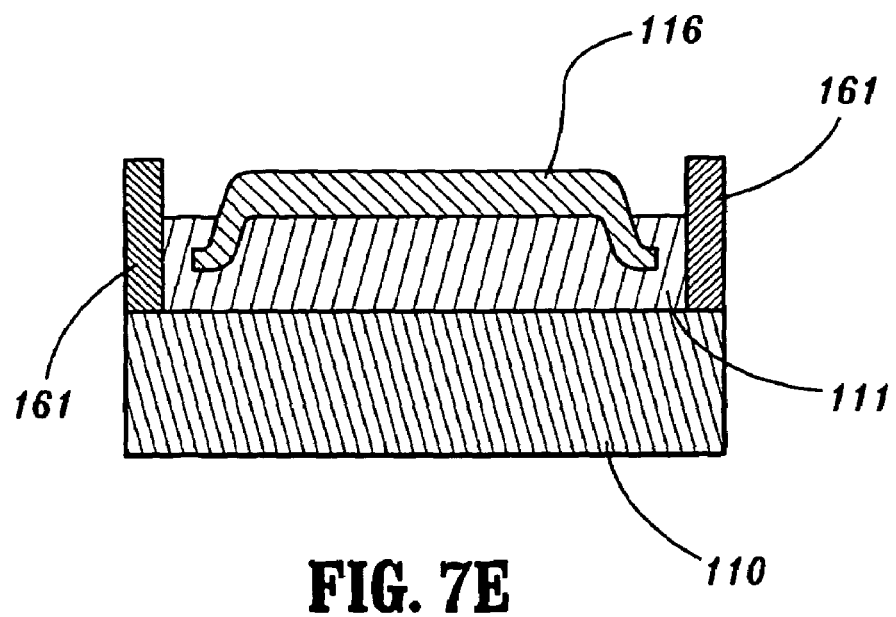
FIG. 7E is a cross section of an electrode configuration showing a compliant barrier disposed about the periphery of the opposing electrodes and insulators which controls/regulates the heat dissipating from the conductive surface.

As best seen in FIG. 7D, the electrode 116 may also include a pinch trim 131 which facilitates secure, integral engagement of the insulate 111 and the electrically conductive surface 116 during the assembly and/or manufacturing process. FIG. 7E shows another embodiment of the present disclosure wherein a compliant material 161 is disposed about the outer peripheries of the electrically conductive surfaces 116, 126 and the substrates 111, 121. it is envisioned that the compliant material 161 acts as a mechanical barrier by restricting heat and steam emanating from the surface thereby reduces thermal spread to surrounding tissue. One or more barriers 161 may be attached to the end effectors 22, 24 and/or the insulting substrate 111, 121 depending upon a particular purpose of to achieve a particular result.

FIGS. 14A, 14B, 14C and 15 show the electrically conducive surfaces 116, 126 raised relative to the insulative coatings or insulators 111, 121. Preferably, the electrically surface 116, 126 is radiused or curved which reduces current concentration and the dissipation of stray currents to surrounding tissue structures. It is contemplated that the insulators 111, 121 and electrically conductive surfaces 116, 126 can be dimensioned to meet at or generally along interfaces or adjoining longitudinally-oriented edges 129, 139 which are radiused to reduce current concentrations 141 and current dissipation proximate the interfaces 129, 139 and opposing electrically conductive surfaces 116, 126.

Figure 12:
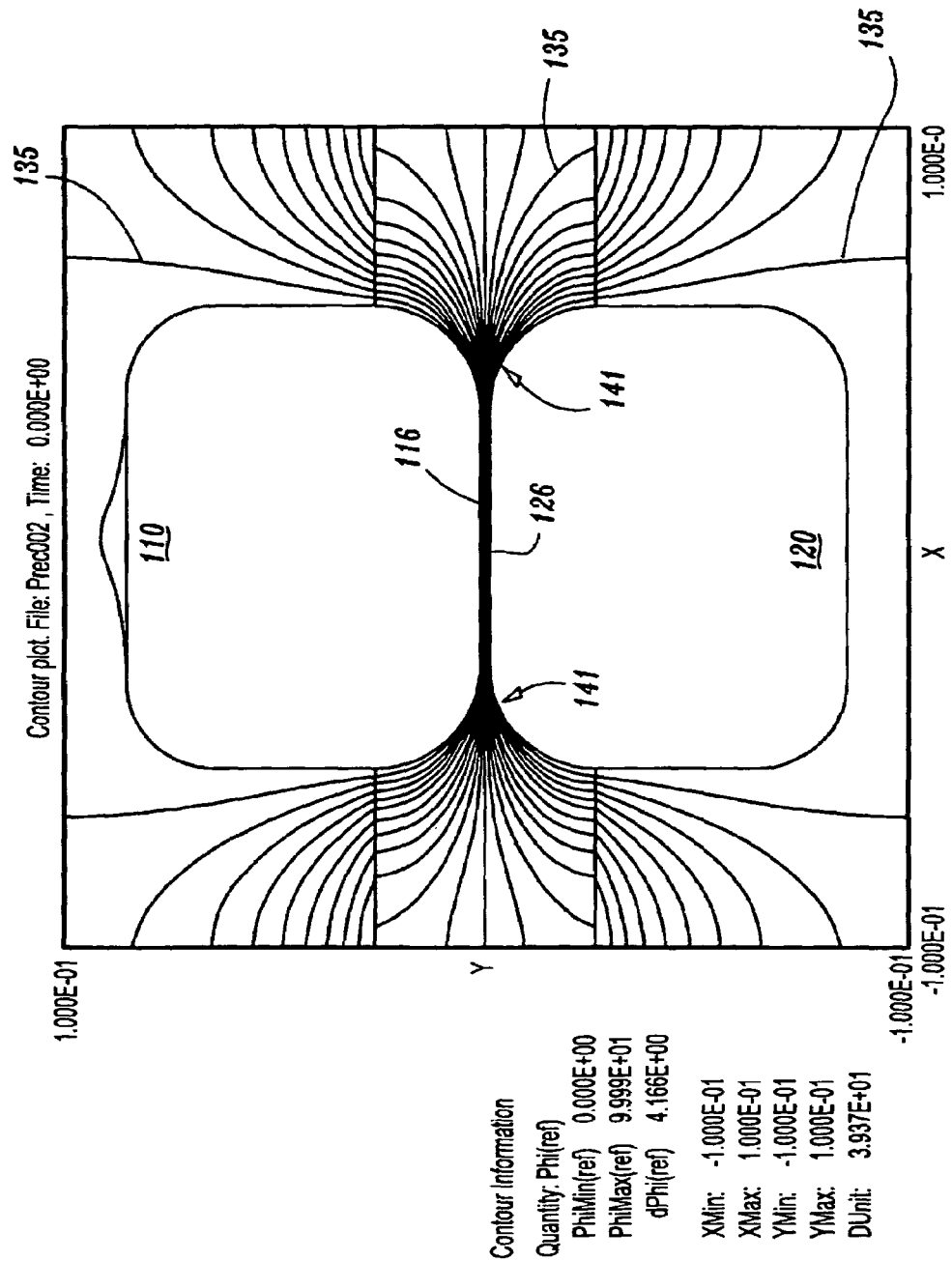
FIG. 12 is a contour plot showing the dissipation of the electrosurgical current across the tissue using an electrode without insulation.

For example and by way of illustration, FIGS. 12 and 13A–13C show other electrode 110, 120 configurations which are known in the prior art. FIG. 12 shows an example of uninsulated (i.e., without insulators 111, 121) opposing electrodes 110, 120 during activation illustrating the electrical field distribution 135 emanating from the opposing electrically conductive surfaces 116, 126 (it is known that current flows perpendicular to these electrical field lines). As can be appreciated, the electrical field 135 emanates well beyond the intended treatment site which can contribute to increased collateral tissue damage and possibly cutting.

Figure 13A:
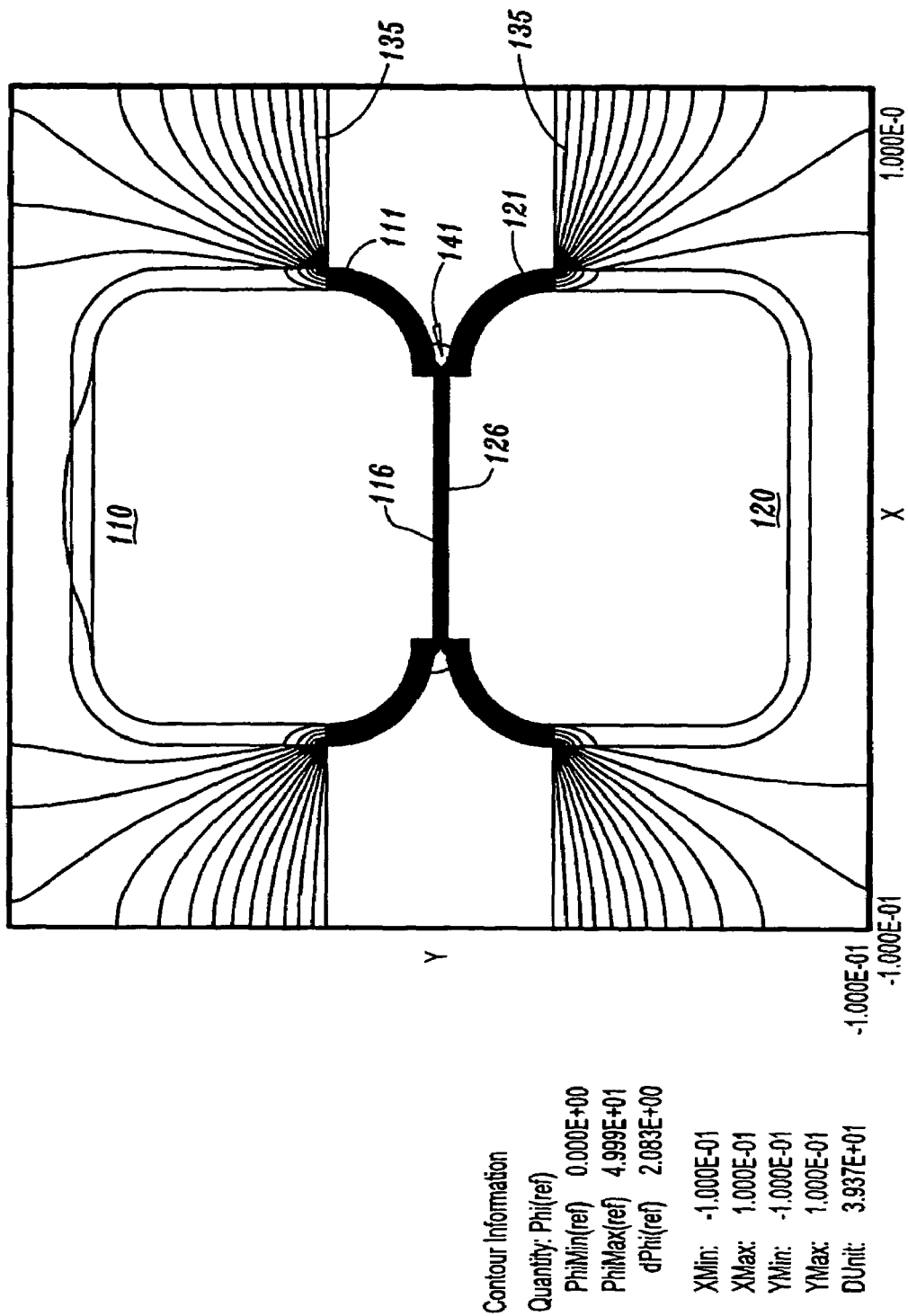
FIG. 13A is a contour plot showing the dissipation of the electrosurgical current across the tissue using an electrode with flush insulator.
Figure 13B:
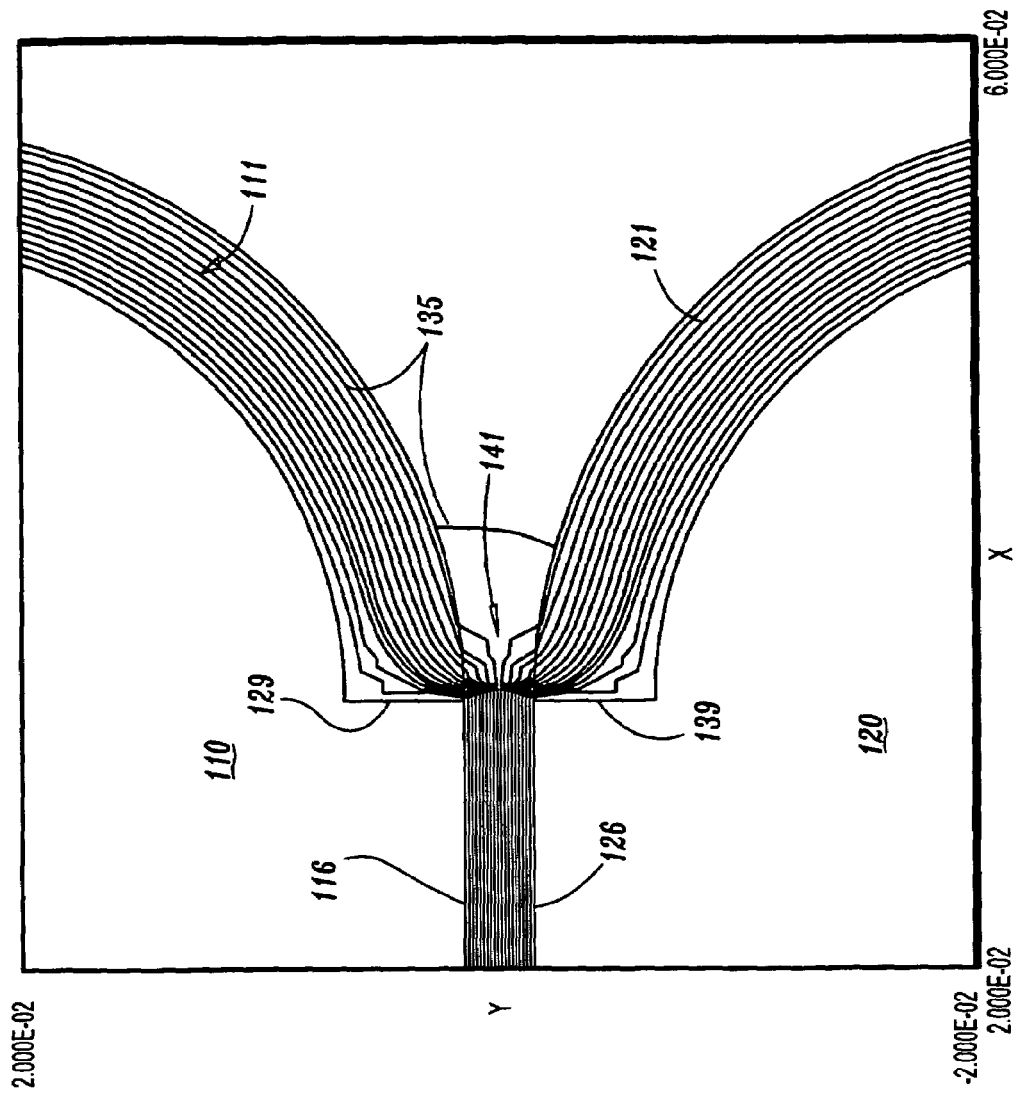
FIG. 13B is an enlarged contour plot of FIG. 13A showing the current concentration and relative dissipation of the electrosurgical current at an adjoining edge or interface between the insulator and the electrically conductive surface.
Figure 13C:
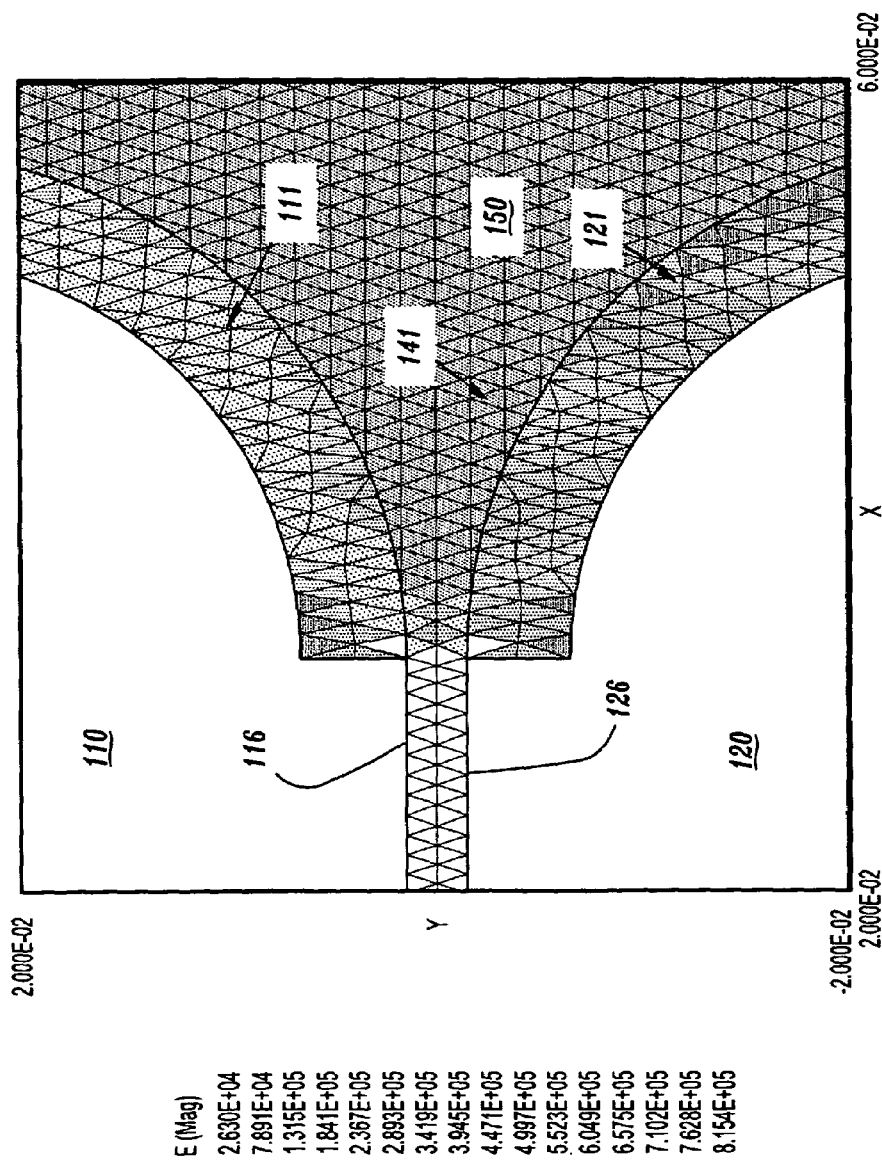
FIG. 13C is an enlarged electrical field magnitude plot of the electrode configuration of FIG. 13A showing the current concentration and relative dissipation of the electrosurgical field distribution at an adjoining edge or interface between the insulator and the electrically conductive surface.

By providing insulators 111, 121 which are flush with the electrically conductive surfaces 116, 126 as shown in FIGS. 13A–13C, the electrical field distribution 135 can be significantly reduced.

However, as the enlarged view of FIGS. 13B and 13C illustrate, a current concentration 141 tends to develop between opposing electrically conductive surfaces 116, 126 and at or proximate interfaces 129, 139.

This current concentration 141 may also lead to negative effects and possibly cause cutting of the tissue or sticking of the tissue to the electrode or electrically conductive surfaces at this site.

Figure 14A:
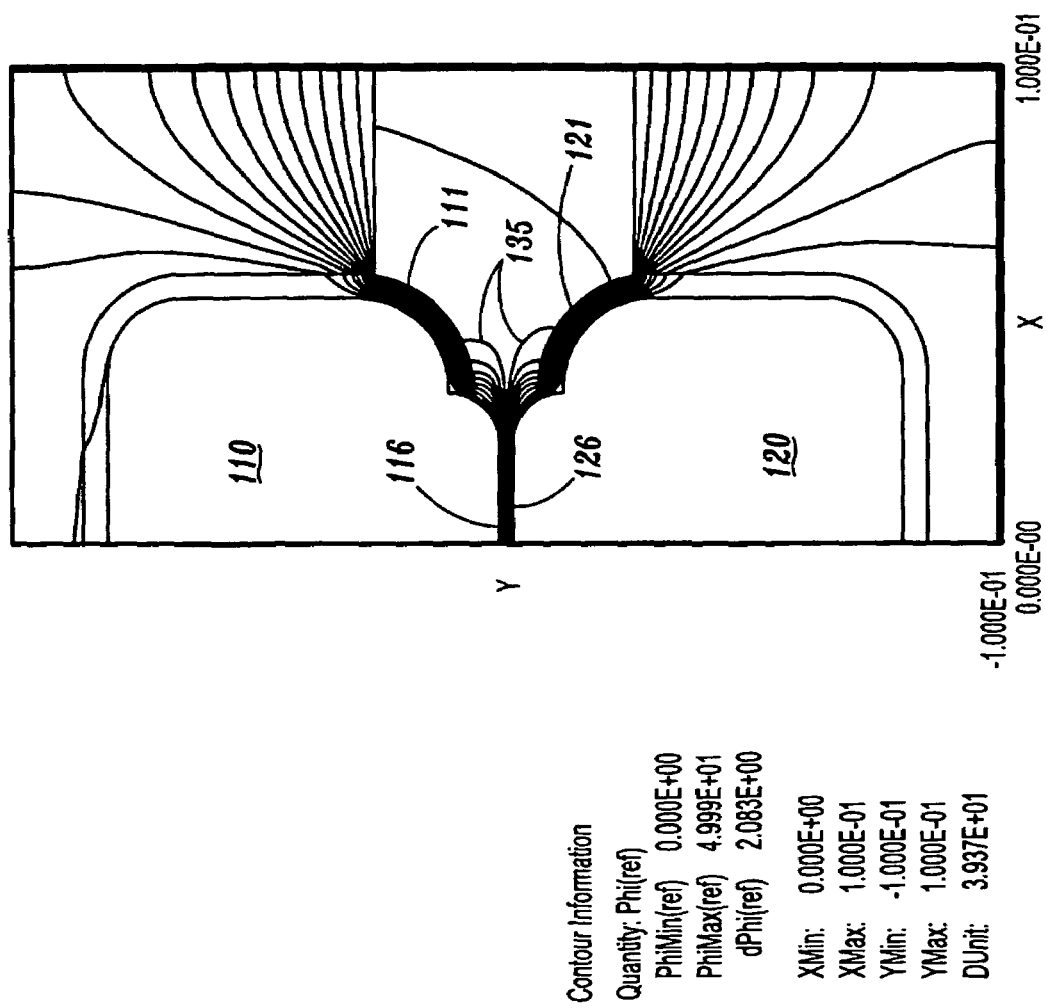
FIG. 14A is a contour plot showing the dissipation of the electrosurgical current across the tissue using an electrode with a raised electrically conductive surface and a radiused interface between the electrically conductive surface and the insulator.
Figure 14B:
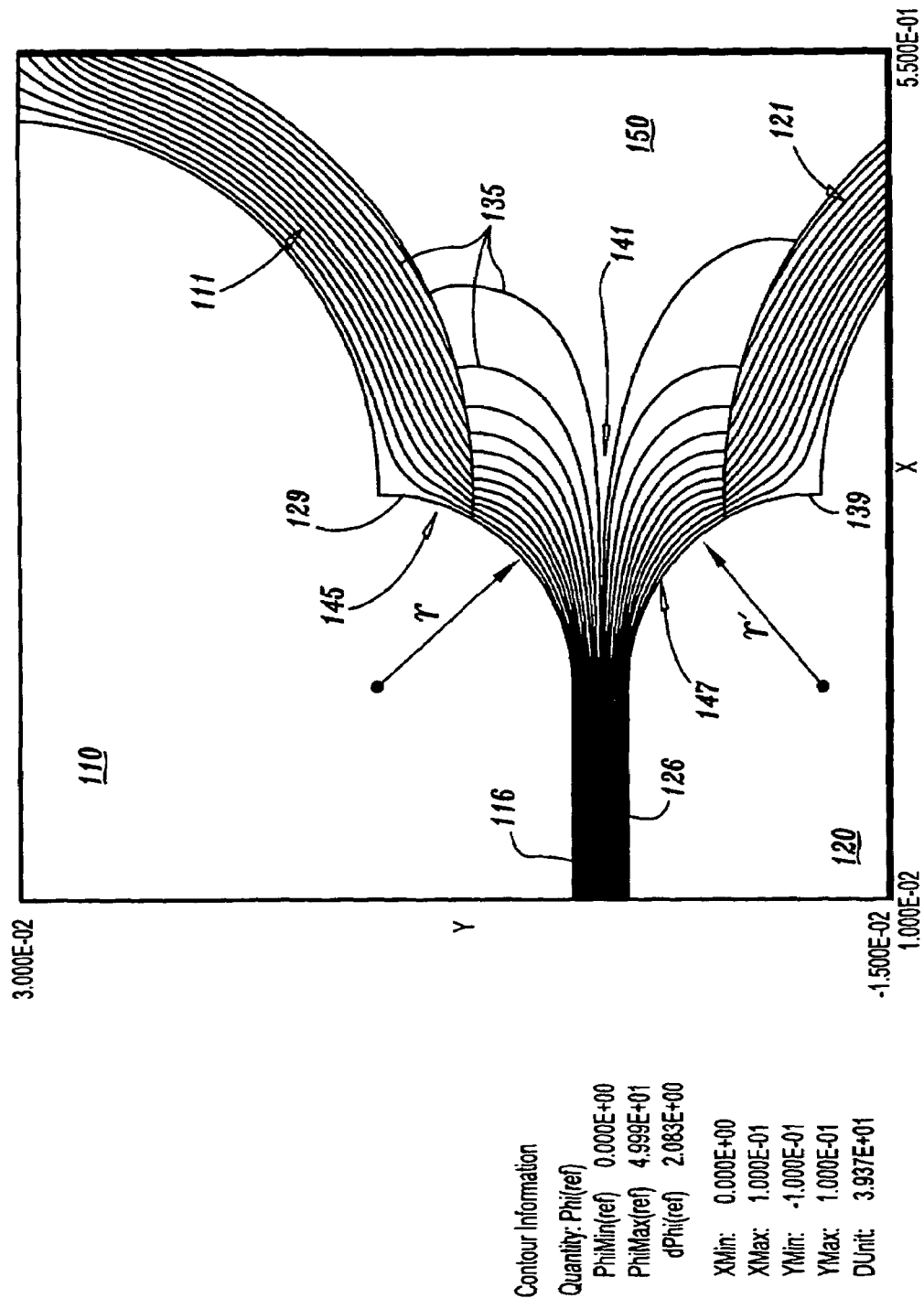
FIG. 14B is an enlarged contour plot of FIG. 14A showing the current concentration and relative dissipation of the electrosurgical current at an adjoining edge or interface between the insulator and the electrically conductive surface.
Figure 14C:
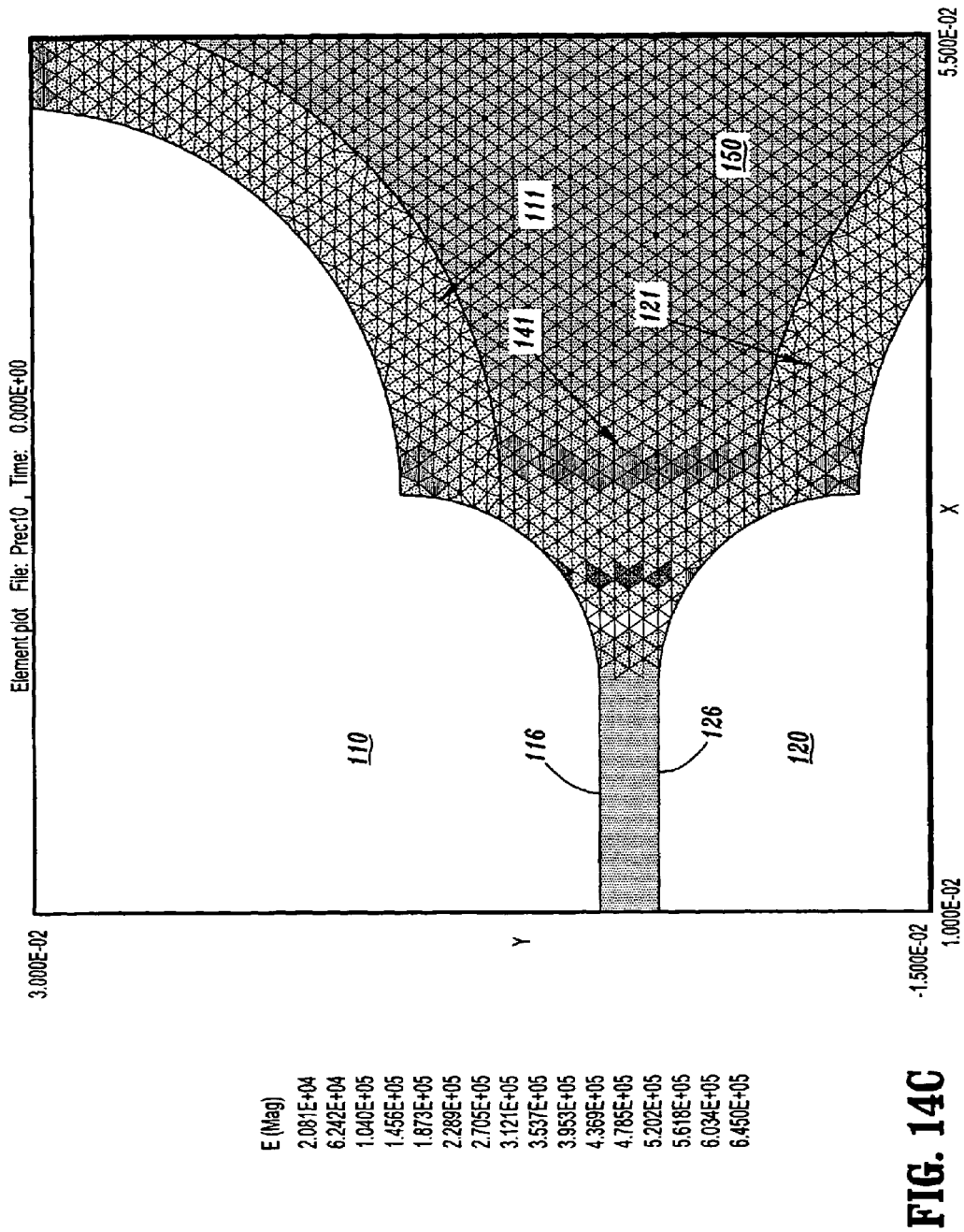
FIG. 14C is an enlarged electrical field magnitude plot of the electrode configuration of FIG. 14A showing the current concentration and relative dissipation of the electrosurgical field distribution at an adjoining edge or interface between the insulator and the electrically conductive surface.
Figure 15:
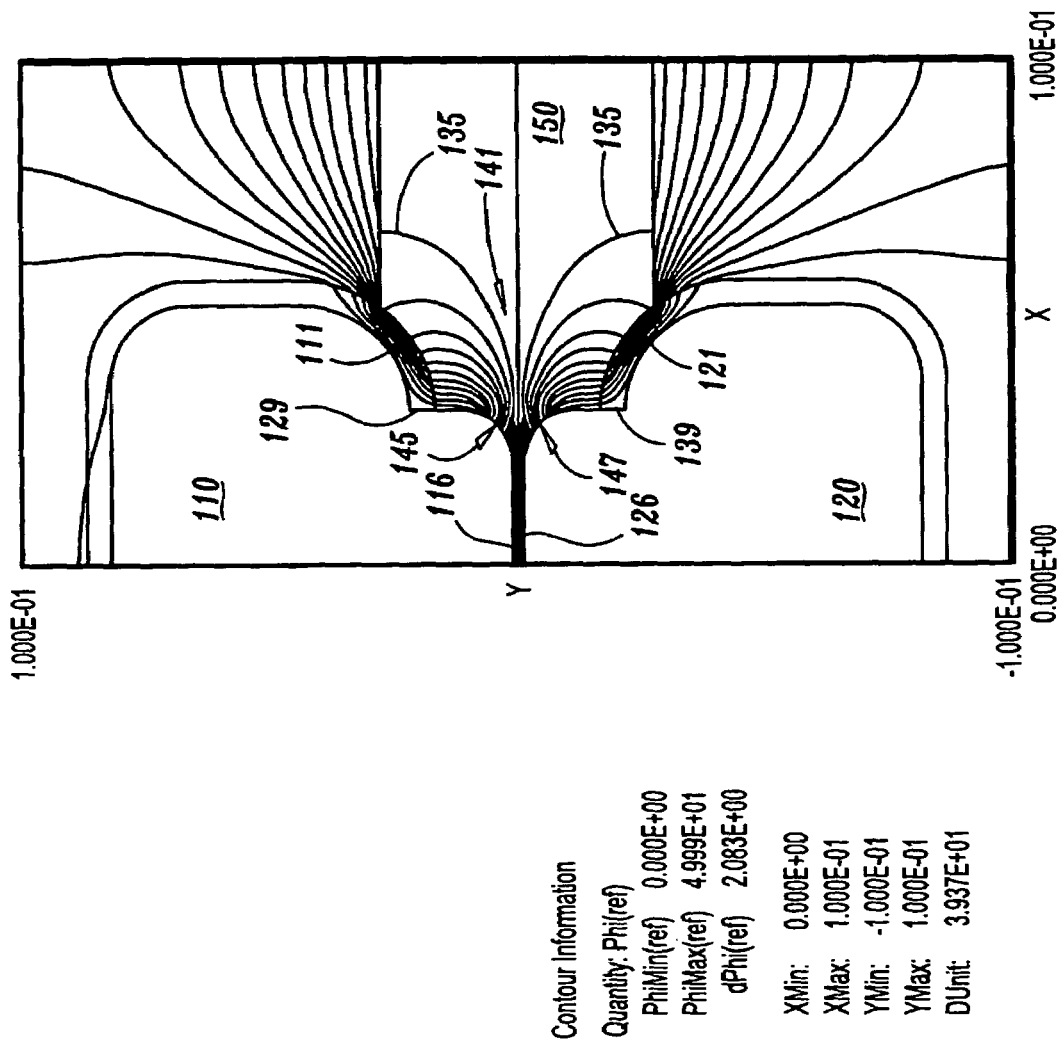
FIG. 15 is a contour plot showing the dissipation of the electrosurgical current across the tissue using an electrode with a raised electrically conductive surface and a ninety degree (90°) interface between the electrically conductive surface and the insulator.

FIGS. 14A–15 show various electrode 110, 120 configurations according to the present disclosure in which the electrically conductive surfaces 116, 126 and the insulators 111, 121 are designed to reduce the amount of current concentration 141 between opposing electrodes 110, 120. More particularly, FIGS. 14A and 14B show a pair of raised electrically conductive surfaces 116, 126 (relative to the insulators 111, 121) which include outer peripheries 145, 147 having radii "r" and "r'", respectively. Preferably, insulators 111, 121 meet outer peripheries 145, 147 and form adjoining edges or interfaces 129, 139 which track along radii "r" and "r'", respectively. It is contemplated that configuring the electrodes 110, 120 in this manner will effectively reduce the current concentration 141 between the outer peripheries 145, 147 of the opposing electrically conductive surfaces 116, 126. As can be appreciated, configuring the electrically conductive surfaces 116, 126 and insulators 111, 121 with this unique profile, additionally provides a more uniform, consistent and more easily controllable electrical field distribution 135 across the adjacent tissue structures. Turning back to FIG. 7C, it is envisioned that insulator 111 may also meet outer periphery 145 in a generally tangential fashion about radius "r". Again, this profile also tends to reduce current concentration and thermal spread and may also contribute to a reduction in the incidence of flashover.

FIG. 15 also shows the insulators 111, 121 and the electrically conductive surfaces 116, 126 meeting at an angle of ninety degrees (90°), however, the insulator 111, 121 is positioned further from the radiused edge 145 of the electrically conductive surface 116, 126. It is envisioned that too much exposure of the edge 145 may initiate the formation of new and/or additional stray currents or electrical fields proximate the interface 129, 139 thereby nullifying the benefits of manufacturing the surface 116, 126 with a radiused edge 145.

Preferably, the radius "r" and "r'" of the outer peripheries 145, 147 of the electrically conductive surfaces are about the same and are about ten thousandths of an inch to about thirty thousandths of an inch. However, it is contemplated that each radii "r" and "r'" may be sized differently depending upon a particular purpose or to achieve a desired result.

Although it is contemplated that geometric modification of the insulator 111 relative to the electrically conductive sealing surface 116 reduces the incidence of flashover and thermal spread, in some cases it may be preferable to simply utilize a different material for the insulator to reduce flashover and thermal spread. For example and with particular respect to flashover, it is known that all plastics have a different resistance to flashover which is commonly measured using a Comparative Tracking Index (CTI). The CTI value required to resist flashover is typically dictated in part by the maximum voltage of the electrosurgical generator, however, other parameters such as frequency also typically effect flashover.

It has been found that in lieu of or in addition to changing the geometry of the insulator 111 and/or conductive surface 116, a plastic insulation can be employed having a CTI value of about 300 to about 600 volts. Examples of high CTI materials include nylons and syndiotactic polystryrenes such as QUESTRA® manufactured by DOW Chemical. Other materials may also be utilized either alone or in combination to reduce flashover, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

In some cases, however, it may be preferable to alter both the geometry of the insulator 111 and/or conductive surface 116 and/or utilize a plastic insulation that does not have a CTI value of about 300 to about 600 volts. Alternatively, certain coatings can be utilized either alone or in combination with one of the above manufacturing techniques to reduce flashover and thermal spread.

Figure 10:
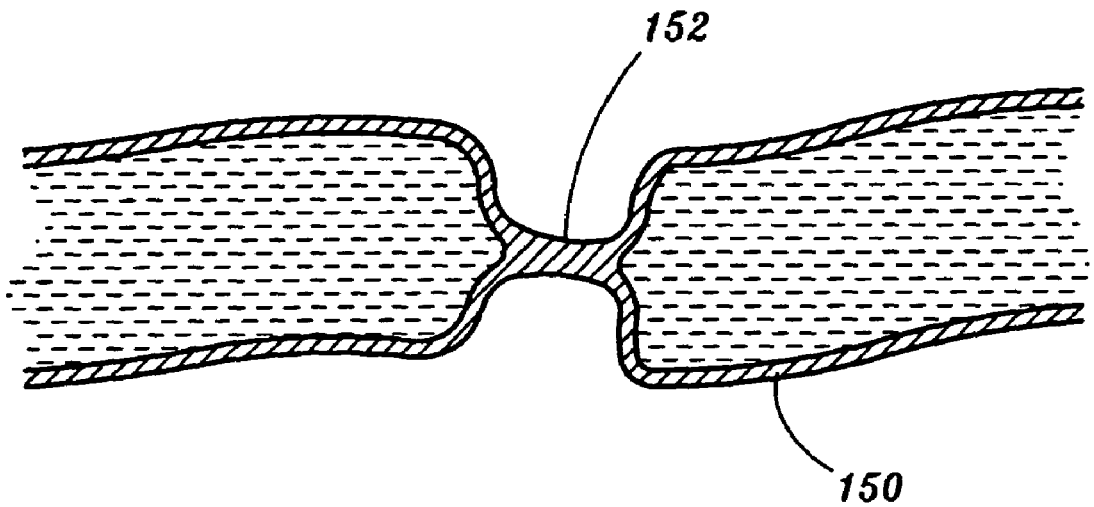
FIG. 10 is a longitudinal cross-section of the sealing site taken along line 10—10 of FIG. 9.
Figure 11:
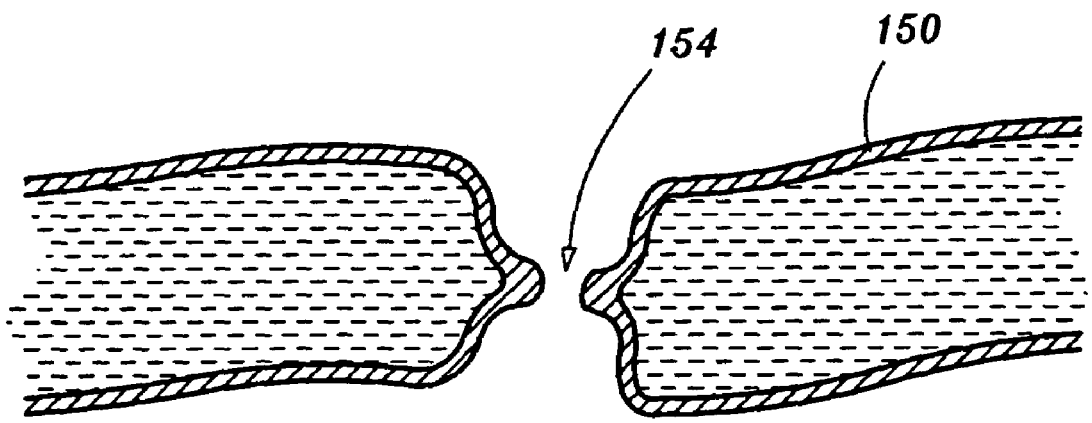
FIG. 11 is a longitudinal cross-section of the sealing site of FIG. 9 after separation of the tubular vessel.

FIG. 8A shows one embodiment of the present disclosure which shows a bipolar forceps 10 during use wherein the handle members 16 and 18 are moved closer to one another to apply clamping force to the tubular tissue 150 to effect a seal 152 as shown in FIGS. 9 and 10. Once sealed, the tubular vessel 150 can be cut along seal 152 to separate the tissue 150 and form a gap 154 therebetween as shown in FIG. 11. Alternatively, the electrically conductive surfaces 116, 126, electrodes 110, 120 and/or the jaw members 42, 44 may be dimensioned as shearing surfaces which effectively cut the tissue when the jaw members 42, 44 are moved relative to one another.

Figure 8B:
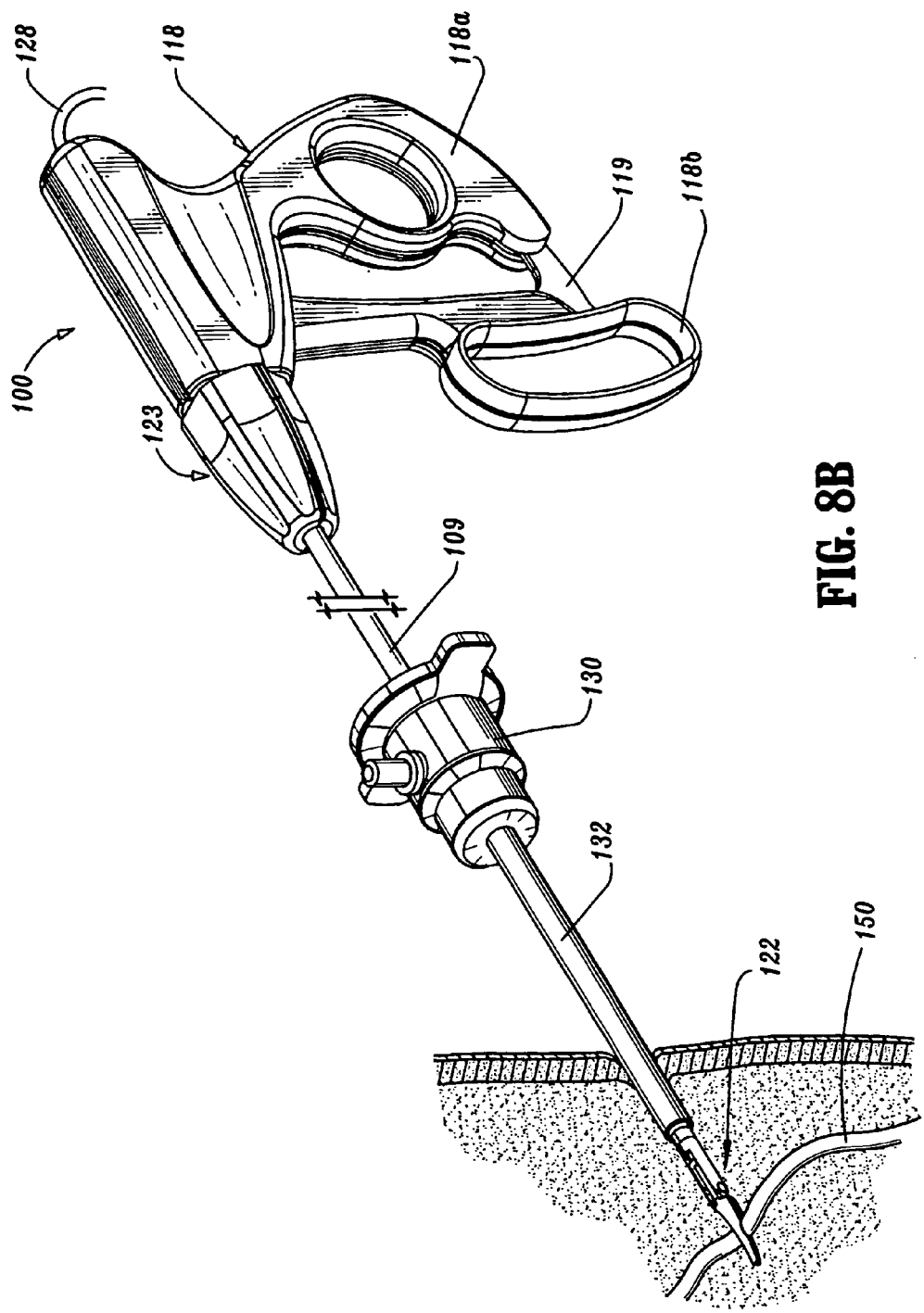
FIG. 8B is a perspective view of an endoscopic version of the present disclosure showing the operative motion of the instrument.

After the bipolar forceps 10 is used or if the electrode assembly 21 is damaged, the electrode assembly 21 can be easily removed and/or replaced and a new electrode assembly 21 may be attached to the forceps in a similar manner as described above. It is envisioned that by making the electrode assembly 21 disposable, the electrode assembly 21 is less likely to become damaged since it is only intended for a single operation and, therefore, does not require cleaning or sterilization. As a result, the functionality and consistency of the components, e.g., the electrically conductive surfaces 126, 116 and insulating surfaces 121, 111, will assure a reliable reduction of thermal spread across tissue and/or reduce the incidence of flashover. Alternatively, the entire electrosurgical instrument may be disposable which, again, may contribute to a reduction of thermal spread across tissue and/or reduce the incidence of flashover FIG. 8B shows an endoscopic bipolar instrument 100 during use wherein movement of a handle assembly 128 applies clamping force on the tubular tissue 150 to effect a seal 152 as shown in FIGS. 9–11. As shown, a shaft 109 and the electrode assembly 122 are inserted through a trocar 130 and cannula 132 and a handle assembly 118 is actuated to cause opposing jaw members of the electrode assembly 122 to grasp tubular vessel 150 therebetween. More particularly, a movable handle 118b is moved progressively towards a fixed handle 118a which, in turn, causes relative movement of the jaw members from an open, spaced-apart position to a closed, activation position. A rotating member 123 allows the user to rotate the electrode assembly 122 into position about the tubular tissue 150 prior to activation. Again, the electrically conductive surfaces 116, 126, electrodes 110, 120 and/or the jaw members 42, 44 may be dimensioned as shearing surfaces which effectively cut the tissue when the jaw members 42, 44 are moved relative to one another.

After the jaw members are closed about the tissue 150, the user then applies electrosurgical energy via connection 128 to the tissue 150. By controlling the intensity, frequency and duration of the electrosurgical energy applied to the tissue 150, the user can either cauterize, coagulate/desiccate, seal, cut and/or simply reduce or slow bleeding with minimal collateral or thermal damage to surrounding tissue and with minimal incidence of flashover.

From the foregoing and with reference to the various figure drawings, those skilled in the art will appreciate that certain modifications can also be made to the present disclosure without departing from the scope of the present disclosure. For example, although it is preferable that electrodes 110 and 120 meet in parallel opposition, and, therefore, meet on the same plane, in some cases it may be preferable to slightly bias the electrodes 110 and 120 to meet each other at a distal end such that additional closure force on the handles 16 and 18 is required to deflect the electrodes in the same plane.

It is envisioned that the outer surface of the end effectors may include a nickel-based material, coating, stamping, metal injection molding which is designed to reduce adhesion between the end effectors (or components thereof) with the surrounding tissue during activation.

While only one embodiment of the disclosure has been described, it is not intended that the disclosure be limited thereto, as it is intended that the disclosure be as broad in scope as the art will allow and that the specification be read likewise. Therefore, the above description should not be construed as limiting, but merely as exemplifications of a preferred embodiment. Those skilled in the art will envision other modifications within the scope and spirit of the claims appended hereto.

What is claimed is:

1. A vessel or tissue sealing instrument having opposing end effectors and a handle for effecting movement of the end effectors relative to one another, comprising:
    a housing;
    a pair of electrodes each including an electrically conductive surface each having a first radii and an insulating substrate each having a second radii, the outer radial dimensions of the insulating substrate being different from the outer radial dimensions of the electrically conductive surface to reduce thermal spread to adjacent tissue structures and the insulating substrate is made from a material having a Comparative Tracking Index of about 300 volts to about 600 volts to reduce the incidence of flashover during the sealing process; and
    a compliant material disposed about an outer periphery of at least one of the electrically conductive surfaces.

2. A vessel or tissue sealing instrument according to claim 1 wherein the insulating substrate is selected from the group consisting of nylon, syndiotactic-polystyrene, polybutylene terephthalate, polycarbonate, acrylonitrile butadiene styrene, polyphthalamide, polymide, polyethylene terephthalate, polyamide-imide, acrylic, polystyrene, polyether sulfone, aliphatic polyketone, acetal copolymer, polyurethane, nylon with polyphenylene-oxide dispersion and acrylonitrile styrene acrylate.

3. A vessel or tissue sealing instrument according to claim 1 wherein the insulating substrate is mounted to the electrically conductive surface by overmolding a stamped plate.

4. A vessel or tissue sealing instrument according to claim 1 wherein the insulating substrate is mounted to the electrically conductive surface by overmolding a metal injection molded plate.

5. A vessel or tissue sealing instrument according to claim 1 wherein the electrically conductive surface of at least one electrode includes a pinch trim and the insulating substrate extends beyond a periphery of the electrically conductive surface.

6. A vessel or tissue sealing instrument according to claim 1 wherein the insulating substrate of each of the electrodes includes at least one mechanical interface for engaging a complimentary mechanical interface disposed on the corresponding end effector of the instrument.

7. A vessel or tissue sealing instrument according to claim 1 wherein the electrically conductive surfaces of the opposing jaw members cooperate to seal tissue.

8. A vessel or tissue sealing instrument according to claim 1 wherein the electrically conductive surfaces of the opposing jaw members include shearing surfaces which cooperate to cut tissue.

9. A vessel or tissue sealing instrument having a handle and at least one shaft for effecting movement of a pair of opposing end effectors relative to one another, comprising:
    a housing;
    a pair of electrodes each having an electrically conductive surface having a first geometric shape and an insulating substrate having a second geometric shape, the electrodes being integrally associated with the end effectors of the instrument such that the electrodes reside in opposing relation relative to one another; and
    a compliant material disposed about an outer periphery of at least one of the electrically conductive surfaces,
    wherein the second geometric shape of the insulating substrate is different than the first geometric shape of the electrically conductive surface to reduce thermal spread to adjacent tissue structures and the insulating substrate is made from a material having a Comparative Tracking Index of about 300 volts to about 600 volts to reduce the incidence of flashover during the sealing process.

* * * * *